US012788504B2

(12) United States Patent
Murray et al.

(10) Patent No.: US 12,788,504 B2
(45) Date of Patent: Nov. 10, 2026

(54) FLUOROSCOPY IMAGING DEVICES, SYSTEMS, AND RELATED METHODS

(71) Applicant: GLOBUS MEDICAL, INC., Audubon, PA (US)

(72) Inventors: Patrick Murray, Collegeville, PA (US); George Yacoub, Lansdale, PA (US); Nicholas Meadows, Langhorne, PA (US); Rohan Vijayan, Olney, MD (US)

(73) Assignee: Globus Medical, Inc., Audubon, PA (US)

( * ) Notice: Subject to any disclaimer, the term of this patent is extended or adjusted under 35 U.S.C. 154(b) by 261 days.

(21) Appl. No.: 18/406,343

(22) Filed: Jan. 8, 2024

(65) Prior Publication Data

US 2025/0221777 A1 Jul. 10, 2025

(51) Int. Cl.
*A61B 34/30* (2016.01)
*A61B 34/10* (2016.01)
(Continued)

(52) U.S. Cl.
CPC .............. *A61B 34/30* (2016.02); *A61B 34/10* (2016.02); *A61B 90/37* (2016.02); *A61B 90/39* (2016.02);
(Continued)

(58) Field of Classification Search
CPC ......... A61B 34/30; A61B 90/39; A61B 90/50; A61B 90/37; A61B 34/10; A61B 2034/207; A61B 2090/3764; A61B 2090/363; A61B 2034/2055; A61B 2034/105; A61B 6/584; A61B 6/487; A61B 6/547; A61B 6/4441; A61B 6/4405; A61B 2034/2059; A61B 2034/2048; A61B 6/583; A61B 34/20; A61B 2017/00725; A61B 2090/3966; A61B 6/0492; A61B 6/582; A61B 2090/376; A61B 2090/364; A61B 2017/00707; A61B 90/36; A61B 2034/2051; A61B 2034/102; A61B 2034/108; A61B 6/022; A61B 6/4464; A61B 6/12; A61B 6/08; A61B 5/055; A61B 6/5258; A61B 5/7267; A61B 6/5235; A61B 6/032; A61B 2034/2065; A61B 2090/3983; A61B 2090/3954; A61B 2034/2072; A61B 5/0205; A61B 5/1123; A61B 5/1071; A61B 5/1079; A61B 5/4561; A61B 5/1077; A61B 90/00; A61B 17/15; A61B 17/17; G06T 7/74; G06T 7/337; G06T 7/248; G06T 2207/30008; G06T 2207/10116; G06T 5/80; G06T 7/0014; G06T 7/80; G06T 12/10; G06T 2207/10081; G06T 2207/20; G06T 2207/30004; G06T 2207/30204;
(Continued)

(56) References Cited

U.S. PATENT DOCUMENTS

| | | | |
|---|---|---|---|
| 6,379,043 B1 * | 4/2002 | Zylka | A61B 6/547 378/207 |
| 10,194,995 B2 * | 2/2019 | Neo | A61B 34/20 |

(Continued)

*Primary Examiner* — Irakli Kiknadze

(57) ABSTRACT

Disclosed herein are spinal fixtures, a robotic system including the spinal fixtures, and related methods for performing spinal procedures including fixing and tracking fixture devices to register patient anatomy in a three-dimensional tracking space.

14 Claims, 28 Drawing Sheets

(51) Int. Cl.
*A61B 34/20* (2016.01)
*A61B 90/00* (2016.01)
*A61B 90/50* (2016.01)

(52) U.S. Cl.
CPC ........ *A61B 90/50* (2016.02); *A61B 2034/105* (2016.02); *A61B 2034/2055* (2016.02); *A61B 2034/207* (2016.02); *A61B 2090/363* (2016.02); *A61B 2090/3764* (2016.02)

(58) Field of Classification Search
CPC ............. G06T 7/75; G06T 2207/10124; G06T 2207/10121; G06T 2207/30244; G06T 2207/10072; G06T 7/70; G06T 2207/20016; G06T 2207/20024; G06T 2207/20081; G06T 2207/20084; G06T 2207/30208; G06T 2207/10088; G16H 20/40; G16H 50/20; G16H 10/60; A61F 2002/4633; A61N 5/1049; A61N 2005/1062; A61N 2005/1061; A61N 2005/1059; A61N 5/1069; A61N 2005/1076; G06V 10/255; G06V 10/82; G06V 2201/03; G06V 10/245; G16B 50/30; G16B 20/00; G06N 5/022; G06N 20/20; G06N 20/00; G06N 3/0464; G06N 3/09; G06N 3/045; G06F 16/906
USPC ....................................... 378/18, 54, 62, 207
See application file for complete search history.

(56) References Cited

U.S. PATENT DOCUMENTS

| | | | | |
|---|---|---|---|---|
| 2002/0041655 | A1* | 4/2002 | Mitschke | A61B 6/547 378/207 |
| 2003/0219102 | A1* | 11/2003 | Mitschke | A61B 6/584 378/207 |
| 2018/0098715 | A1* | 4/2018 | Deitz | A61B 34/10 |
| 2019/0201106 | A1* | 7/2019 | Siemionow | G06V 10/82 |
| 2020/0286222 | A1* | 9/2020 | Essenreiter | G06T 7/0012 |
| 2021/0321877 | A1* | 10/2021 | Fields | A61B 6/466 |

* cited by examiner

1500

3600

FLUOROSCOPY IMAGING DEVICES, SYSTEMS, AND RELATED METHODS

TECHNICAL FIELD

The subject matter described herein relates generally to medical devices, and in particular, to robotic fluoroscopy imaging devices, systems and related methods.

BACKGROUND

Various medical procedures require localization of a three-dimensional position of a surgical instrument within the body in order to effect optimized treatment. For example, some surgical procedures to fuse vertebrae require that a surgeon drill multiple holes into the bone structure at specific locations. To achieve high levels of mechanical integrity in the fusing system, and to balance the forces created in the bone structure, it is necessary that the holes are drilled at the correct location. Vertebrae, like most bone structures, have complex shapes including non-planar curved surfaces, making accurate and perpendicular drilling difficult. Conventionally, a surgeon manually holds and positions a drill guide tube by using a guidance system to overlay the position of the drill guide tube onto a three dimensional image of the bone structure. This manual process is tedious and error prone, such that the success of the surgical procedure may largely depend upon the surgeon's dexterity. A robotic surgical platform can assist surgeons to position surgical instruments and perform surgical procedures on a patient.

It is desirable to provide improved instruments, systems and methods for use during robot-assisted surgical procedures, to more accurately position surgical instruments and depict the positions of those instruments in relation to anatomical structures of the patient. Improved localization accuracy can minimize human and robotic error while allowing fast and efficient surgical process. The ability to perform operations on a patient with a robotic surgical platform and computer software can enhance the overall surgical procedure and results achieved for the patient.

SUMMARY

All aspects, examples and features mentioned below can be combined in any technically possible way.

An aspect of the disclosure provides a system comprising: a medical imaging device comprising an x-ray source and an x-ray detector configured to generate a plurality of images based on x-rays received at the x-ray detector from the x-ray source; a fixture coupled to the medical imaging device between the x-ray source and the x-ray detector; a calibration phantom coupled to the fixture and configured to calibrate the medical imaging device based on known, simulated bone mineral density (BMD) of material disposed therein, wherein the calibration phantom comprises a first material having a first simulated BMD, and a second material having a second simulated BMD; and a medical navigation system operatively coupled with the medical imaging device, the fixture, and the calibration phantom, wherein the medical navigation system is configured to register the plurality of images from the medical imaging device to a three-dimensional tracking space.

Another aspect of the disclosure provides a registration fixture for use with a medical navigation system for registration of a plurality of images to a three-dimensional tracking space, comprising: a frame configured to be coupled with a medical imaging device; an x-ray opaque fiducial pattern comprising a plurality of radiopaque markers disposed in the frame and operatively coupled with the medical imaging device, wherein the x-ray opaque fiducial pattern; a first calibration phantom comprising a first material having a first simulated bone mineral density (BMD) disposed in the frame; and a second calibration phantom comprising a second material having a second simulated BMD disposed in the frame.

Another aspect of the disclosure provides a method comprising: using a medical imaging device, capturing a plurality of images of a patient before a surgery; selecting an anatomical location on the patient to fixate a merge fixture; using a three-dimensional printer, manufacturing the merge fixture to complement a contour of the anatomical location on the patient; dissecting the patient at the anatomical location; attaching the merge fixture to the patient at the anatomical location; tracking a position of the merge fixture with an optical sensor; and calculating position and orientation of anatomy of the patient based on position and orientation of the merge fixture at the anatomical location.

Two or more aspects described in this disclosure, including those described in this summary section, may be combined to form implementations not specifically described herein.

The details of one or more implementations are set forth in the accompanying drawings and the description below. Other features, objects and advantages will be apparent from the description and drawings, and from the claims.

BRIEF DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings:

FIG. 12A illustrates lowering the reflective marker onto the marker post, while FIG. 12B illustrates the marker fully seated on the post, in accordance with embodiments of the disclosure.

Figure 1:
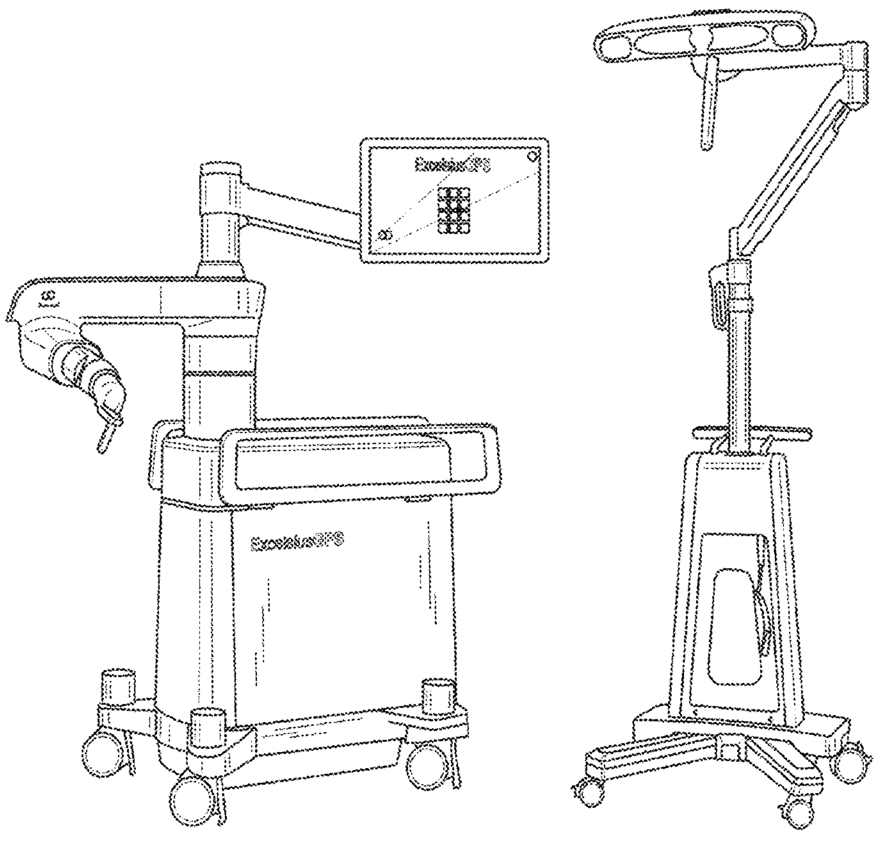
FIG. 1 illustrates a robotic system that includes a robotic base station and a camera stand, in accordance with embodiments of the disclosure.

It is noted that the drawings of the subject matter are not necessarily to scale. The drawings are intended to depict only typical aspects of the subject matter, and therefore, should not be considered as limiting the scope of the disclosed subject matter. In the drawings, like numbering represents like elements between the drawings.

DETAILED DESCRIPTION

The following discussion is presented to enable a person skilled in the art to make and use embodiments of the present disclosure. Various modifications to the illustrated embodiments will be readily apparent to those skilled in the art, and the principles herein can be applied to other embodiments and applications without departing from embodiments of the present disclosure. Thus, the embodiments are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of the embodiments. Skilled artisans will recognize the examples provided herein have many useful alternatives and fall within the scope of the embodiments.

As described herein, a robotic navigation computer system enables real-time surgical navigation using radiological patient images and guides the trajectory of specialized surgical instruments along a surgeon-specified path using a robotic arm. The system software reformats patient-specific CT images acquired before surgery, or fluoroscopic images acquired during surgery, and displays them on screen from a variety of views. Prior to operating, the surgeon may then create, store, access, and simulate trajectories. During surgery, the system guides the instruments to follow the trajectory specified by the user, and tracks the position of surgical instruments in or on the patient anatomy and continuously updates the instrument position on these images. The surgery is performed by the surgeon, using the specialized surgical instruments. The software can also show how the actual position and path during surgery relate to the pre-surgical plan, and help guide the surgeon along the planned trajectory. While the surgeon's judgment remains the ultimate authority, real-time positional and trajectory information obtained from the robotic navigation computer system can validate this judgment. An example robotic navigation computer system that could be used with embodiments herein is the ExcelsiusGPS® robotic navigation platform (Globus Medical, Inc., Audubon, PA, USA).

The robotic navigation computer system is a robotic positioning system that includes a computer controlled robotic arm, hardware, and software that enables real time surgical navigation and robotic guidance using radiological patient images (pre-operative CT, intra-operative CT and fluoroscopy), using a dynamic reference base and positioning camera. The navigation and guidance system determines the registration or mapping between the virtual patient (points on the patient images) and the physical patient (corresponding points on the patient's anatomy). The term "registration" as used herein refers to the process of determining the coordinate transformations from one coordinate system to another based on medical images. Once this registration is created, the software displays the relative position of a tracked instrument, including, e.g., the end-effector of the robotic arm, on the patient images. This visualization can help guide the surgeon's planning and approach. As an aid to visualization, the surgeon can plan implant placement on the patient images prior to surgery. The information contained in the plan coupled with the registration provides the necessary information to provide visual assistance to the surgeon during free hand navigation or during automatic robotic alignment of the end-effector.

During surgery, the system tracks the position of GPS compatible instruments, including the end-effector of the robotic arm, in or on the patient anatomy and continuously updates the instrument position on patient images utilizing optical tracking. Standard non-navigated metallic instruments that fit through the guide tube at the selected trajectory may be used without navigation while the guide tube is stationary, for uses such as bone preparation (e.g. rongeurs, reamers, etc.) or placing minimally invasive spinal implants (e.g. rod inserters, locking cap drivers, etc.) that are not related to screw placement. Navigation can also be performed without guidance. System software is responsible for all motion control functions, navigation functions, data storage, network connectivity, user management, case management, and safety functions. In various embodiments, robotic navigation computer system surgical instruments are non-sterile, re-usable instruments that can be operated manually or with the use of the positioning system.

Robotic navigation computer system instruments may include registration instruments, patient reference instruments, surgical instruments, and end-effectors. Registration instruments incorporate arrays of reflective markers, and are used to track patient anatomy and surgical instruments and implants. Components include the verification probe, surveillance marker, surgical instrument arrays, intra-op CT registration fixture, fluoroscopy registration fixture, and dynamic reference base (DRB). Patient reference instruments are either clamped to or driven into any appropriate rigid anatomy that is considered safe and provides a point of rigid fixation for the DRB. Surgical instruments are used to prepare the implant site or implant the device such as, e.g., awls, drills, drivers, taps, probes, etc. End-effectors can be wirelessly powered guide tubes that attach to the distal end of the robotic arm and provide a rigid structure for insertion of surgical instruments.

The robotic navigation computer system is intended for use as an aid for precisely locating anatomical structures and for the spatial positioning and orientation of instrument holders or tool guides to be used by surgeons for navigating or guiding standard surgical instruments in open or percutaneous procedures. The system is indicated for any medical condition in which the use of stereotactic surgery may be appropriate, and where reference to a rigid anatomical structure, such as e.g., the skull, a long bone, or vertebrae can be identified relative to a CT-based model, fluoroscopy images, and/or digitized landmarks of the anatomy.

As used herein, the term "screw" is used interchangeably with, and is considered equivalent to and synonymous with the terms: bone fastener, fastener, fixation screw, spinal fixation screw, bone anchor, and pedicle screw. The term driver is used interchangeably with, and is considered equivalent to and synonymous with a screw driver, or any device that drives insertion of a bone anchor as would be understood by one skilled in the art. Use of the term proximal refers to the direction away from attachment of an element to the subject, while use of the term distal refers to the direction opposite the proximal direction and toward attachment of an element to the subject. The terms "user" and "surgeon" are used interchangeably with one another, as are the terms "patient" and "subject."

As discussed in detail herein, embodiments of the robotic navigation computer system include four (4) primary components, including: a robotic base station, a camera stand, one or more instruments, and system software. FIG. 1 illustrates a robotic system 100 that includes a robotic base station and a camera stand, as further described herein.

Figure 2:
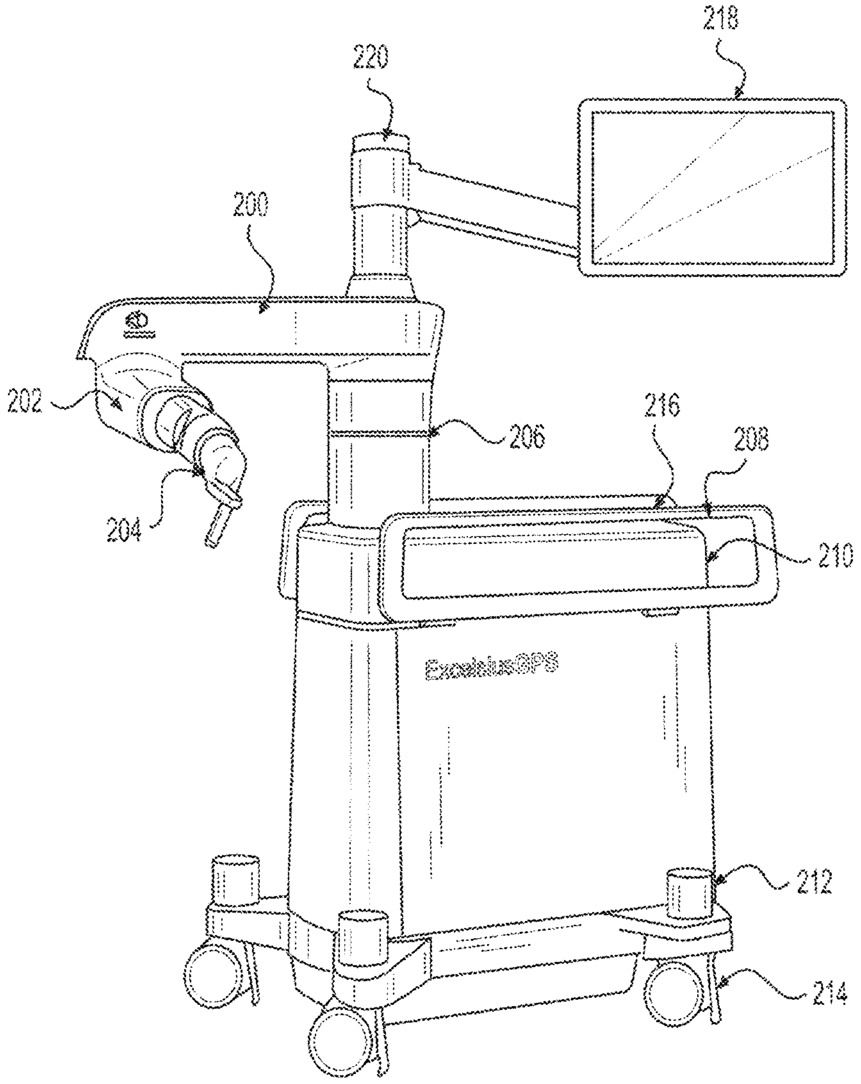
FIG. 2 illustrates components of the robotic base station, in accordance with embodiments of the disclosure.

FIG. 2 illustrates the robotic base station and components thereof, which is the primary control center for the robotic system. As shown, the robotic base station includes an upper arm 200 connected to a lower arm 202. An end-effector 204 is connected to a distal end of the lower arm 202, and serves as the interface between the lower arm 202 and surgical instruments discussed herein. A vertical column 206 is connected to, and physically supports, the upper arm 200 and connected components (i.e., lower arm 202 and end-effector 204).

Figure 3:
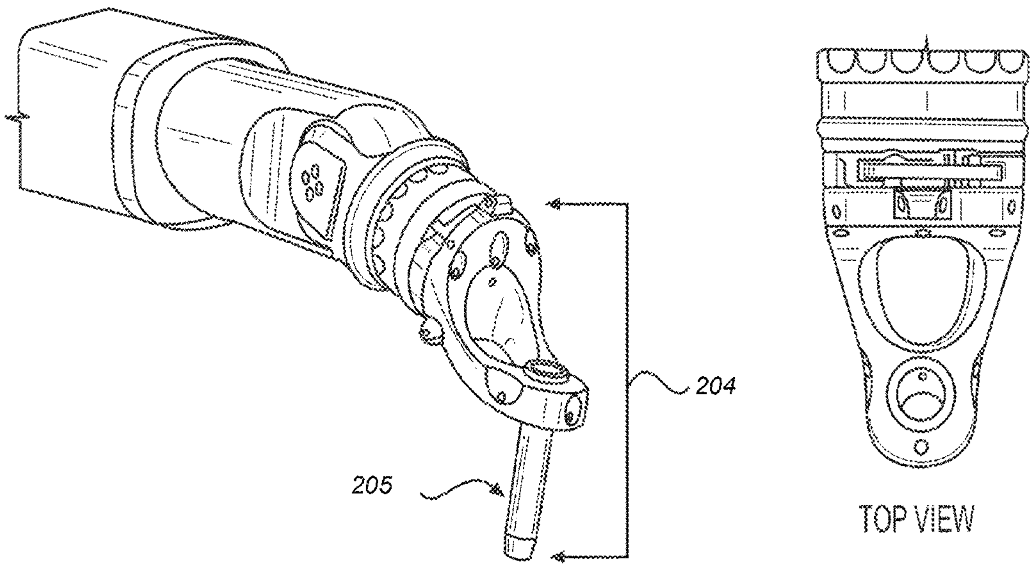
FIG. 3 illustrates isometric and top views of an end-effector attached to a robotic arm of the robotic base station, in accordance with embodiments of the disclosure.

FIG. 3 illustrates an isometric view and a top view of the end-effector 204 according to some embodiments. The end-effector 204 enables a rigid connection (e.g., through a sterile drape during a surgical procedure) to precisely position the respective surgical instrument disposed therein. The end-effector 204 is provided as a separate component of the robotic base station, which is sterilized by the user prior to the surgical procedure, and configured to engage various surgical instruments. The end-effector 204 may be powered wirelessly to drive active markers that can be recognized by the camera stand to identify the location and orientation of the end-effector 204. As shown, the end-effector 204 includes a guide tube 205 configured to receive, or otherwise couple with, at least one surgical instrument.

As further shown in FIG. 2, the robotic base station further includes a control panel 208 and a connector panel 210 which are positioned, e.g., at the rear of the robotic base station. The control panel 208 is configured to display and control system power and general positioning functions. The connector panel 210 is configured to provide one or more ports for electrical coupling with one or more external devices.

Figure 4A:
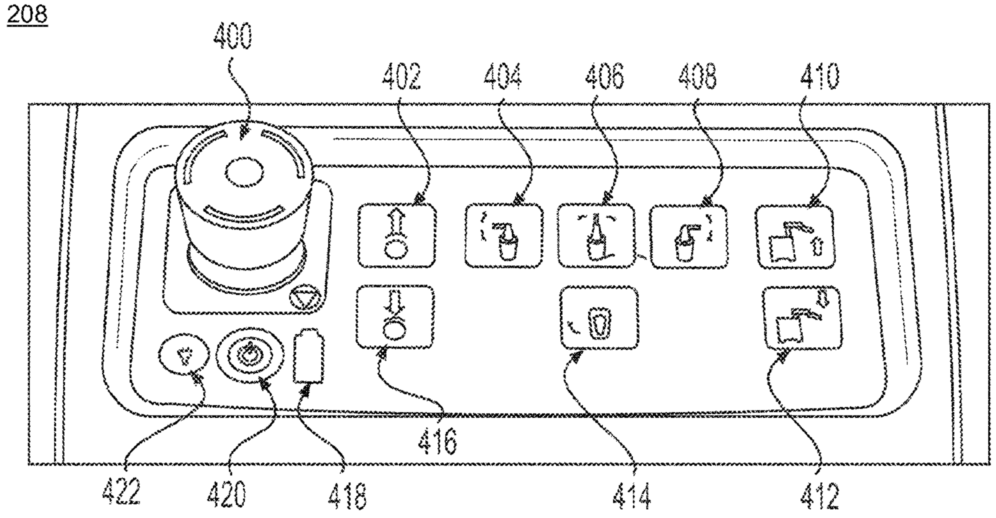
FIG. 4A illustrates a control panel on the rear of the robotic base station.

FIG. 4A illustrates an example embodiment of the control panel 208, including: an emergency stop button 400, a stabilizers disengage button 402, a left position button 404, a straight position button 406, a right position button 408, a vertical column up button 410, a vertical column down button 412, a dock position button 414, a stabilizers engage button 416, a battery status indicator 418, a power button 420, and a line power indicator 422.

Figure 4B:
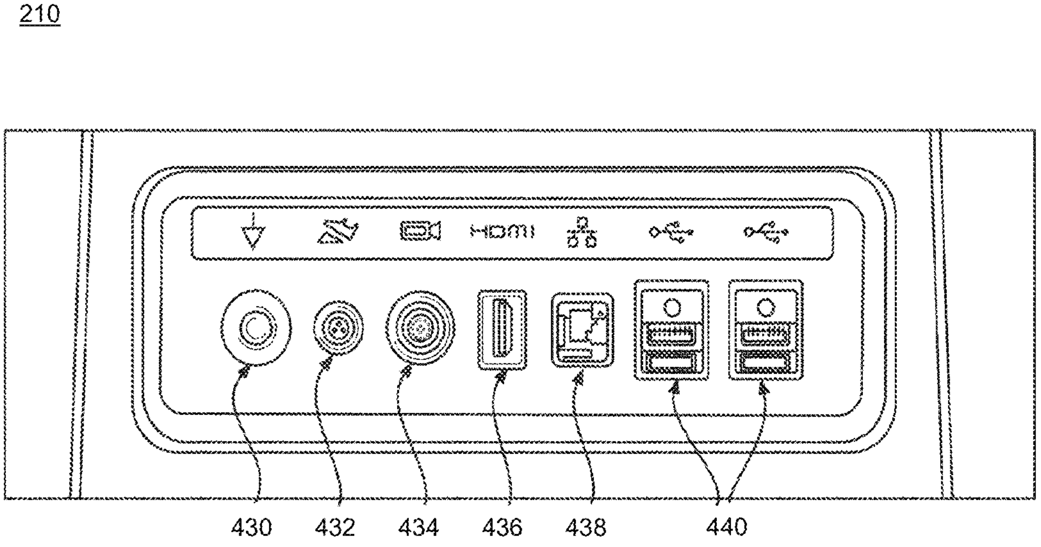
FIG. 4B illustrates a connector panel on the rear of the robotic base station, in accordance with embodiments of the disclosure.

FIG. 4B illustrates an example embodiment of the connector panel 210, including: an equipotential terminal 430, a foot pedal connector 432, a camera connector port 434, an HDMI connector 436, an ethernet connector 438, and dual USB 3.0 ports 440.

As further shown in FIG. 2, the robotic base station further includes stabilizers 212, rolling casters 214, a tablet compartment 216, a monitor 218, and an illumination ring 220. The stabilizers 212 and rolling casters 214 may selectively immobilize the robotic base station during the surgical procedure. The monitor 218 is connected to the vertical column 206 and allows a user (e.g., surgeon) to plan the surgical procedure and to visualize anatomical structures, instruments, and implants in real time. The monitor 218 may include a high resolution, flat panel electronic display such as, e.g., touch screen liquid crystal display (LCD), light-emitting diode (LED) display, organic light-emitting diode display (OLED), quantum dot light-emitting diode (QLED), or combinations thereof. In some embodiments, the position and orientation of the monitor 218 can be manually adjusted to a desired location and orientation. In other embodiments, an actuator (not shown) may be configured to programmatically adjust the position and orientation of the monitor 218 in response to input from the surgeon such as, e.g., a voice command to move the monitor between positions relative to the vertical column. In some embodiments, the robotic base station further includes an external mouse to interact with software displayed via the monitor 218. The tablet compartment 216 is configured to receive a wireless tablet (not shown) therein, which is optionally available for use as a second monitor to facilitate operative planning and software control in conjunction with the monitor 218. The illumination ring 220 is disposed on an upper portion of the vertical column 206, and configured to illuminate in one or more colors corresponding to information about the robotic system such as, e.g., the current status/state of the robotic system. For example, the illumination ring 220 may emit green light indicating the robotic system is ready for use, emit red light indicating an error state, and emit yellow light indicating a state in which user intervention is required before a planned trajectory can proceed.

Figure 5:
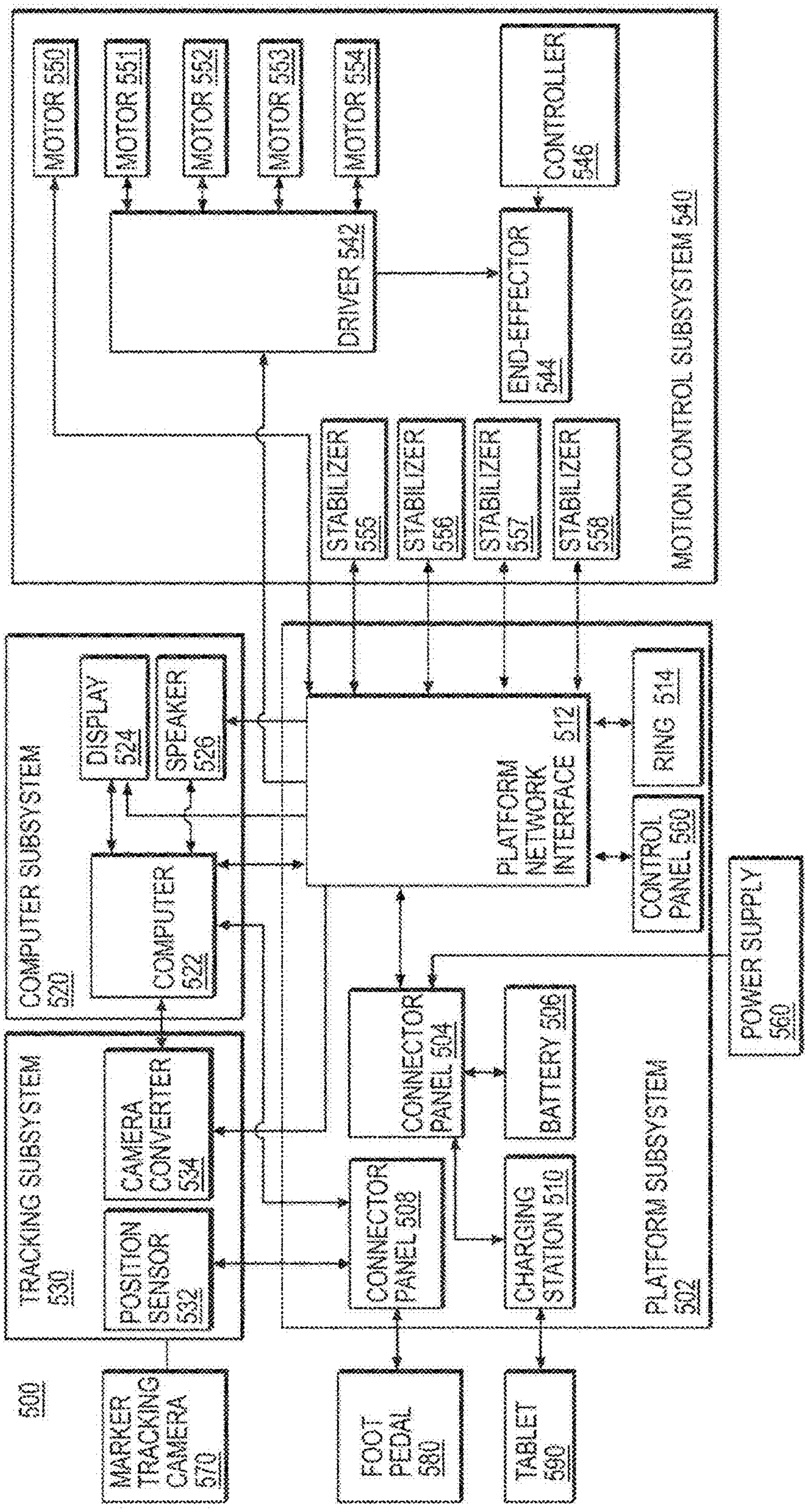
FIG. 5 illustrates a block diagram of electronic components of a robot portion of a robot surgical platform, in accordance with embodiments of the disclosure.

FIG. 5 illustrates a block diagram of electronic components of a robot 500 portion of a robot surgical platform which is configured according to embodiments. In certain embodiments, the robot 500 may be in the form of the robotic base station and components thereof as shown in FIG. 2. The robot 500 can include platform subsystem 502, computer subsystem 520, motion control subsystem 540, and tracking subsystem 530. Platform subsystem 502 can include battery 506, power distribution module 504, platform network interface 512, and tablet charging station 510. Computer subsystem 520 can include computer 522, display 524, and speaker 526. Motion control subsystem 540 can include driver circuit 542, motors 550, 551, 552, 553, 554, stabilizers 555, 556, 557, 558, end-effector 544, and controller 546 (e.g., one or more processors and associated circuitry). Tracking subsystem 530 can include position sensor 532 and camera converter 534 which is connectable to a marker tracking camera 570, e.g., via the platform network interface 512. Robot 500 can include a foot pedal 580 and tablet computer 590.

Input power is supplied to the robot 500 via a power source 560 which may be provided to the power distribution module 504. The power distribution module 504 receives input power and is configured to generate different power supply voltages, which in turn are provided to other modules, components, and subsystems of the robot 500. Power distribution module 504 may be configured to provide different voltage supplies to platform network interface 512, which may be provided to other components such as computer 520, display 524, speaker 526, driver 542 to, for example, power the motors 550, 551, 552, 553, 554 and end-effector 544, ring 514, camera converter 534, and other components for the robot 500 for example, fans for cooling the various electrical components.

Power distribution module 504 may also provide power to other components such as tablet charging station 510 that may be located within a tablet drawer. Tablet charging station 510 may be configured to communicate through a wired and/or wireless interface with tablet 590. Tablet 590 may be used to display images and other information for use by surgeons and other users consistent with various embodiments disclosed herein.

Power distribution module 504 may also be connected to battery 506, which serves as a temporary power source in the event that power distribution module 504 does not receive power from input power 560. At other times, power distribution module 504 may serve to charge battery 506 when needed.

Other components of platform subsystem 502 can include connector panel 508, control panel 516, and ring 514. Connector panel 508 may serve to connect different devices and components to robot 500 and/or associated components and modules. Connector panel 508 may contain one or more ports that receive lines or connections from different components. For example, connector panel 508 may have a ground terminal port that may ground the robot 500 to other equipment, a port to connect foot pedal 580 to robot 500, and/or a port to connect to tracking subsystem 530. The tracking subsystem 530 can include a position sensor 532, camera converter 534, and the marker tracking camera 570 which may be supported by a camera stand. Connector panel 516 can include other ports to allow USB, Ethernet, HDMI communications to other components, such as computer 520.

Control panel 516 may provide various buttons or indicators that control operation of the robot 500 and/or provide information regarding the robot 500. For example, the control panel 516 may include buttons to power on or off robot 500, lift or lower stabilizers 555-558 that may be designed to engage casters to lock the robot 500 from physically moving and/or to raise and lower the robot base and/or a vertical support for the robot arm. Other buttons may control the robot 500 to stop movement of a robot arm in the event of an emergency, which may remove all motor power and apply mechanical and/or electromechanical brakes to stop all motion from occurring. Control panel 516 may also have indicators notifying the user of certain system conditions such as a line power indicator or status of charge for battery 506. In certain embodiments, the control panel 516 may be in the form of the control panel 208 and components thereof as shown in FIGS. 2 and 4A. In certain embodiments, the stabilizers 555-558 and casters may be in the form of the stabilizers 212 and casters 214 as shown in FIG. 2.

Ring 514 may be a visual indicator to notify the user of robot 500 of different modes that robot 500 is operating under and certain warnings to the user. In certain embodiments, the ring 514 may be in the form of the illumination ring 220 as shown in FIG. 2.

Computer 522 of the computer subsystem 520 includes at least one processor circuit (also referred to as a processor for brevity) and at least one memory circuit (also referred to as a memory for brevity) containing computer readable program code. The processor may include one or more data processing circuits, such as a general purpose and/or special purpose processor, e.g., microprocessor and/or digital signal processor. The processor is configured to execute the computer readable program code in the memory circuit to perform operations, which may include some or all of the operations described herein as being performed by a surgical robot and may further perform some or all of the operations described herein as being performed by a surgical implant planning computer.

The program code includes an operating system and software to operate robot 500. Computer 522 may receive and process information from other components (for example, tracking subsystem 530, platform subsystem 502, and/or motion control subsystem 540) in order to display information to the user. Further, computer subsystem 520 may include speaker 526 to provide audio notifications from the computer 522 to the user.

Tracking subsystem 530 can include position sensor 532 and camera converter 534. The position sensor 532 may include the marker tracking camera 570. Tracking subsystem 530 may track the location of markers that are located on the different components of robot 500 and/or instruments used by a user during a surgical procedure. This tracking may be conducted in a manner consistent with the present disclosure which can include the use of infrared technology that illuminates and enables tracking by the camera 570 of the location of active or passive elements, such as LEDs or reflective markers, respectively. The location, orientation, and position of structures having these types of markers may be provided to computer 522 which may be shown to a user on display 524 and/or tablet 590. For example, a surgical instrument or other tool having these types of markers and tracked in this manner (which may be referred to as a navigational space) may be shown to a user in relation to a three dimensional image of a patient's anatomical structure, such as a CT image scan, fluoroscopic image, and/or other medical image. In certain embodiments, the display 524 may be in the form of the display 218, and the table 590 may be stored in the tablet compartment 216, as shown in FIG. 2.

The robot 500 can include a robot base that is coupled to a robot arm which is movable by the motors, e.g., one or more of motors 550-554, relative to the robot base. The robot arm can include an upper arm connected to a vertical support and a lower arm that is rotatably coupled to an end of the upper arm and extends to couple to the end-effector 544. Motion control subsystem 540 may be configured to physically move a vertical column of the robot 500, e.g., raise and lower the robot arm and/or the robot base in a vertical direction, move an upper arm of the robot 500, move a lower arm of the robot 500, and/or rotate the end-effector 544. The physical movement may be conducted through the use of one or more motors 550-554. For example, motor 550 may be configured to vertically lift or lower the robot base and/or the robot arm in a vertical direction. Motor 551 may be configured to laterally move the upper arm around a point of engagement. Motor 552 may be configured to laterally move the lower arm around a point of engagement with the upper arm. Motors 553 and 554 may be configured to move the end-effector 544 in a manner that controls the roll and/or tilt, thereby providing multiple angles that end-effector 544 may be moved. These movements may be performed by controller 546 responsive to commands from the computer 522 and which may control these movements through load cells disposed on the end-effector 544 and activated by a user engaging these load cells to move the end-effector 544 in a desired manner. In certain embodiments, the robot arm may be in the form of the upper arm 200 and the lower arm 202, the end-effector 544 may be in the form of the end-effector 204, and the vertical column may be in the form of the vertical column 206, as shown in FIG. 2.

The robot 500 may augment manual input by a user, e.g., when a user applies force to one or more load cells on the end-effector 544, and/or provide automatic movement of the robot arm. The robot 500 may also augment manual movement by a user and/or provide automatic movement of a vertical column of the robot base. For automatic movement, the computer 522 may respond to receiving input from a user, such as by indicating on display 524 (which may be, e.g., a touchscreen input device) the location of a surgical instrument or component on a three dimensional medical image of the patient's anatomy on the display 524. The computer 522 can control one or more of the motors 550-554 to perform automatic movement of the robot arm along a trajectory that has been computed to move the end-effector 544 based on location of the user's input relative to the medical image. The user may initiate automatic movement by stepping on the foot pedal 580 and/or by manipulating another user interface.

Figure 6:
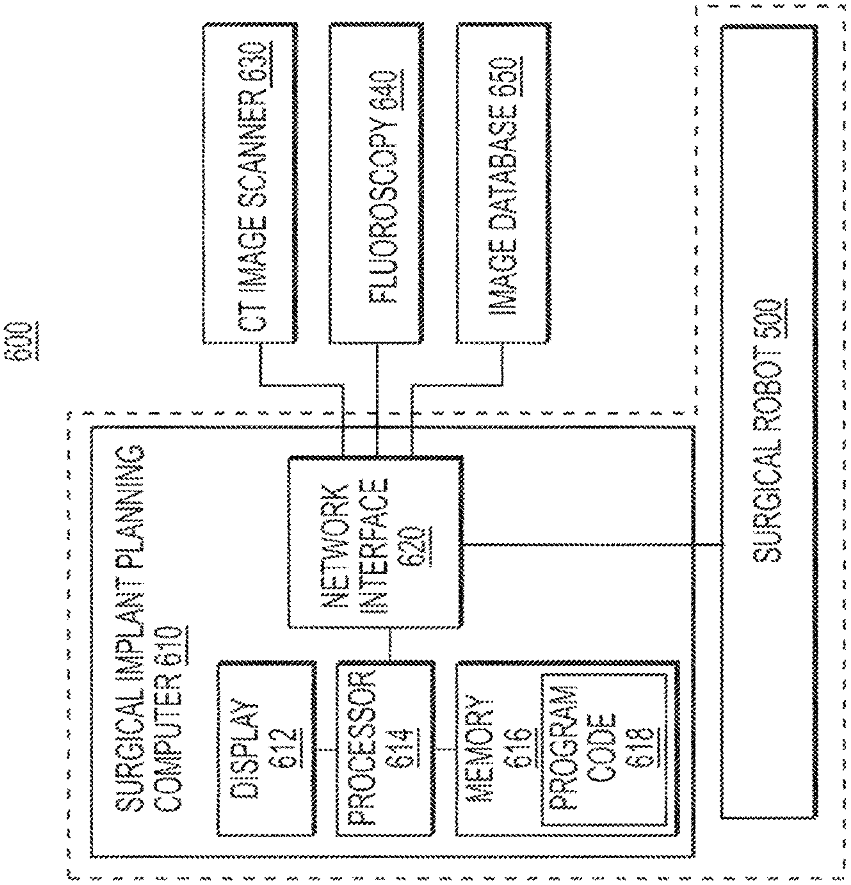
FIG. 6 illustrates a block diagram of a surgical system that includes a surgical implant planning computer which may be separate from and operationally connected to the robot or incorporated therein, in accordance with embodiments of the disclosure.

FIG. 6 illustrates a block diagram of a surgical system 600 that includes a surgical implant planning computer 610 which may be separate from and operationally connected to the robot 500 or at least partially incorporated therein. Alternatively, at least a portion of operations disclosed herein for the surgical implant planning computer 610 may be performed by components of the robot 500 such as by the computer subsystem 520.

Referring to FIG. 6, the surgical implant planning computer 610 includes a display 612, at least one processor circuit 614 (also referred to as a processor for brevity), at least one memory circuit 616 (also referred to as a memory for brevity) containing computer readable program code 618, and at least one network interface 620 (also referred to as a network interface for brevity). The network interface 620 can be configured to connect to a CT image scanner 630, a fluoroscopy image scanner 640, an image database 650 of medical images, components of the robot 500, the marker tracking camera 570, and/or other electronic equipment. When the surgical implant planning computer 610 is at least partially integrated within the robot 500, the display 612 may correspond to the display 524 and/or the tablet 590, the network interface 620 may correspond to the platform network interface 512, and the processor 614 may correspond to the computer 522. The processor 614 may include one or more data processing circuits, such as a general purpose and/or special purpose processor, e.g., microprocessor and/or digital signal processor. The processor 614 is configured to execute the computer readable program code 618 in the memory 616 to perform operations, which may include some or all of the operations described herein as being performed by a surgical implant planning computer. For example, the processor 614 can perform various operations as described and shown in U.S. Pat. No. 10,675,094 B2, the entirety of which is incorporated by reference herein.

Figure 7:
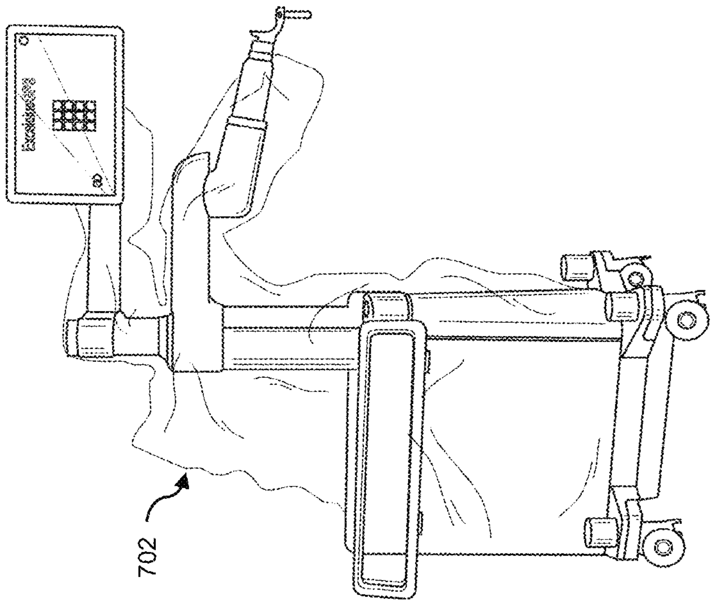
FIG. 7 illustrate the robotic base station draped for a surgical procedure, in accordance with embodiments of the disclosure.

FIG. 7 illustrates an example of the robotic system (i.e., ExcelsiusGPS® robotic navigation platform) draped with a drape 702 in preparation for the surgical procedure.

Figure 8:
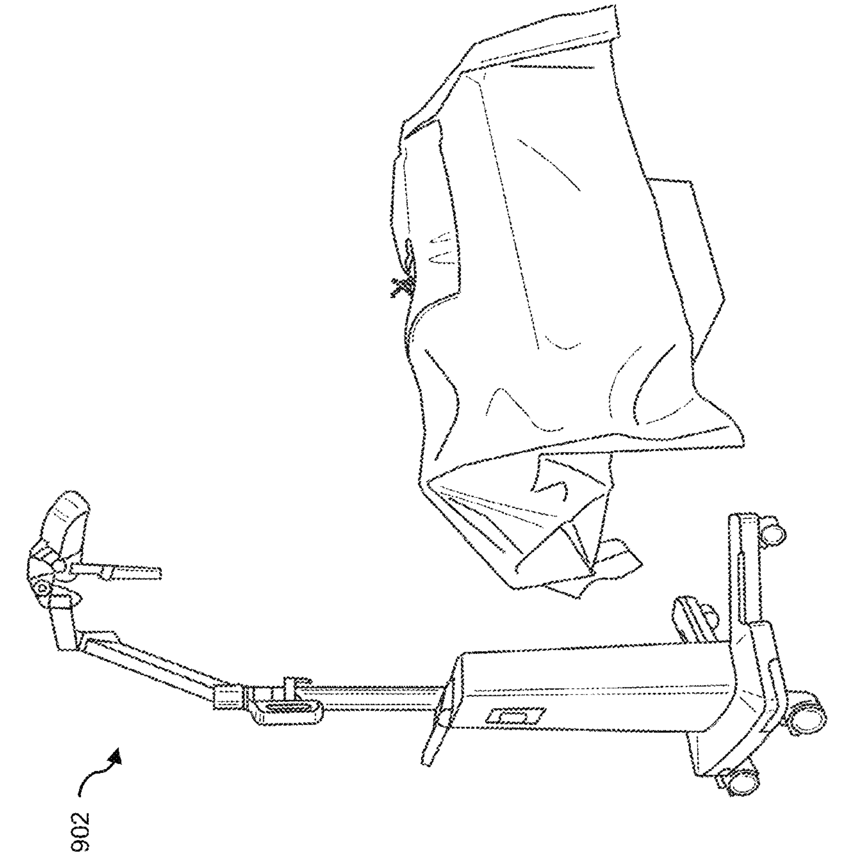
FIG. 8 illustrates positioning the camera stand for a surgical procedure, in accordance with embodiments of the disclosure.
Figure 9:
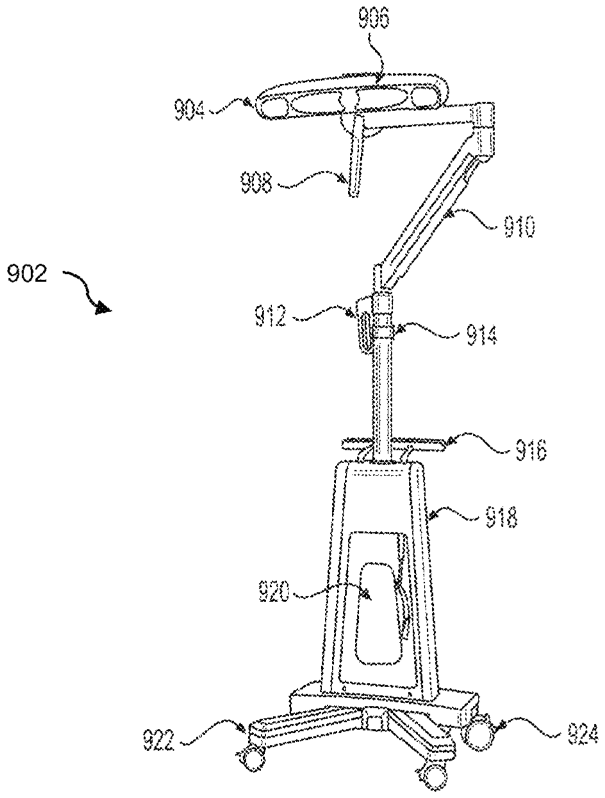
FIG. 9 illustrates features of the camera stand, in accordance with embodiments of the disclosure.
Figure 10:
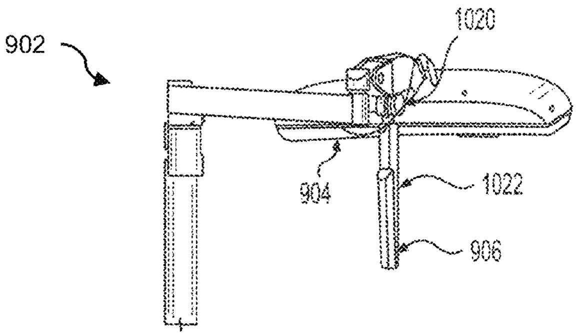
FIG. 10 illustrates a rear view of the camera stand showing alignment buttons, in accordance with embodiments of the disclosure.

With reference to FIGS. 8-10, perspective views of a camera stand 902 are illustrated. FIG. 8 shows the camera stand 902 being positioned proximate to the patient during a surgical procedure. The camera stand 902 is mobile and adjusts in order to position a camera 904 (FIG. 9) such that a field of view of the camera 904 includes the operating field and optical markers within the operating field, as discussed herein. As shown in FIG. 9, the camera stand 902 includes: the camera 904; a camera laser alignment light 906; a positioning handle 908; a support arm 910; a height adjustment handle 912; a locking handle 914; a docking handle 916; a release handle 918; a cable holder 920; legs 922; and casters 924. As shown in FIG. 10, the camera stand 902 further includes alignment buttons such as, e.g., a handle tilt button 1020 and a laser button 1022. As will be described in greater detail below, the robotic system can include one or more tracking markers configured to track the movement of the robot arm, end-effector, patient, and/or surgical instruments in three dimensions. For example, the camera 904 may be used to track reflective markers disposed on a dynamic reference base (DRB), such as an array.

Figure 11:
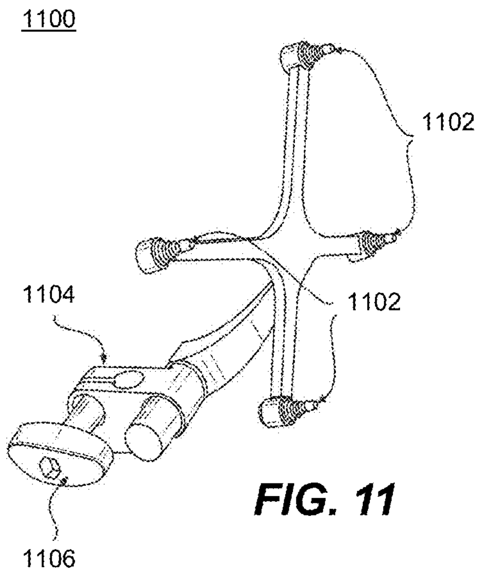
FIG. 11 illustrates a dynamic reference base, in accordance with embodiments of the disclosure.
Figure 12A:
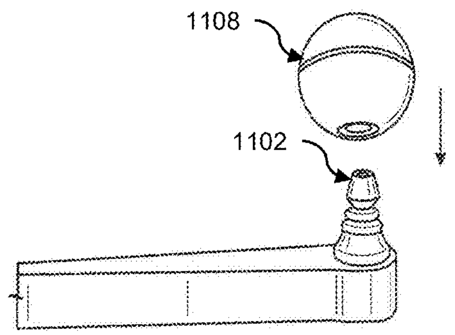
FIGS. 12A and 12B illustrate steps in a process of attaching a reflective marker to a marker post.
Figure 12B:
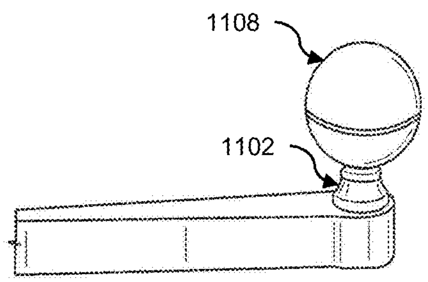

FIG. 11 illustrates a dynamic reference base (DRB) 1100 according to some embodiments. The DRB 1100 may include an array with four (4) marker posts 1102, each configured to receive a reflective marker thereon which allows an optical sensor such as, e.g., the camera 904, to track the location during a surgical procedure. FIGS. 12A and 12B illustrate the placement of a reflective marker 1112 onto a marker post 1102. As further shown in FIG. 11, the marker posts 1102 are connected to a compression clamp 1104 which is operated by a DRB knob 1106. The DRB 1100 may be attached to surgical instruments and fixtures via the compression clamp 1104 and DRB knob 1106 as discussed herein. It should be noted that DRB 1100 is shown by way of example, and other DRB configurations may additionally or alternatively be used within the scope of the present disclosure. For example, the DRB can include any combination of features as described and shown, inter alia, in U.S. Pat. No. 11,253,216 B2, the entirety of which is incorporated by reference herein.

Figure 13:
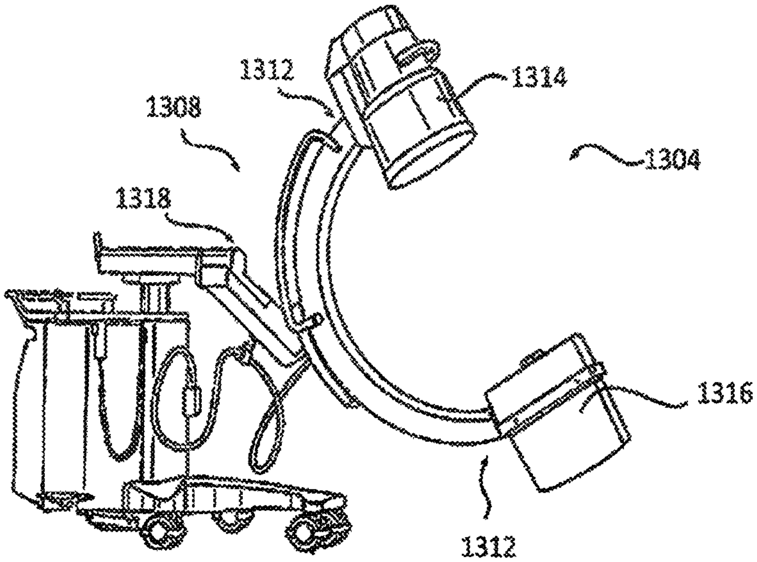
FIGS. 13 and 14 illustrate embodiments of medical imaging devices, in accordance with embodiments of the disclosure.
Figure 14:
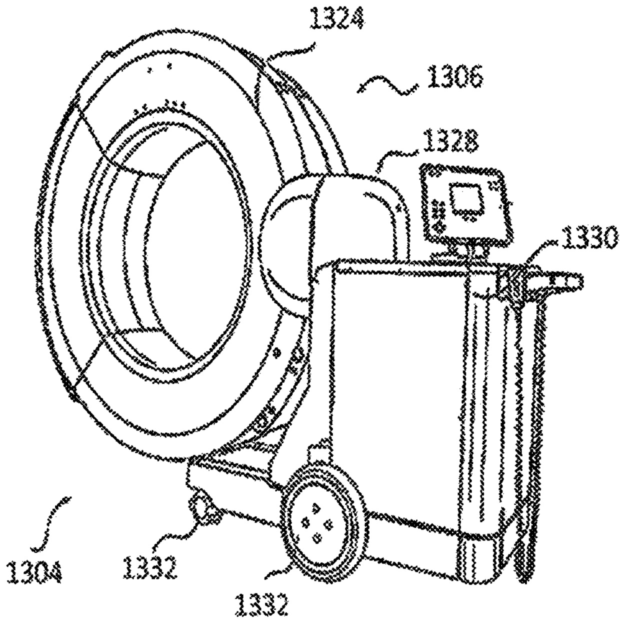

Referring now to FIGS. 13 and 14, medical imaging systems are shown which may be used in conjunction with robotic systems described herein, to acquire pre-operative, intra-operative, post-operative, and/or real-time image data of patient anatomy. Any appropriate subject matter may be imaged for any appropriate procedure using a medical imaging system 1304. The medical imaging system 1304 may be any imaging device such as medical imaging device 1306 and/or a C-arm 1308 device. It may be desirable to take x-rays of patient anatomy from a number of different positions, without the need for frequent manual repositioning of the patient which may be required in an x-ray system. As illustrated in FIG. 13, the medical imaging system 1304 may be in the form of a C-arm 1308 that includes an elongated C-shaped member terminating in opposing distal ends 1312 of the "C" shape. The C-arm 1308 may further include an x-ray source 1314 and an x-ray detector 1316 (also referred to as an image receptor). The space within the C-arm 1308 may provide room for the physician to attend to the patient substantially free of interference from x-ray support structure 1318. As illustrated in FIG. 14, the imaging system may include medical imaging device 1306 having a gantry housing 1324 attached to a support structure 1328, such as a wheeled mobile cart 1330 with wheels 1332, which may enclose an image capturing portion (not shown). The image capturing portion may include an x-ray source and/or emission portion and an x-ray receiving and/or image receiving portion, which may be disposed about one hundred and eighty degrees from each other and mounted on a rotor (not shown) relative to a track of the image capturing portion. The image capturing portion may be operable to rotate three hundred and sixty degrees during image acquisition. The image capturing portion may rotate around a central point and/or axis, allowing image data of the patient to be acquired from multiple directions or in multiple planes. Although certain medical imaging systems 1304 are exemplified herein, it will be appreciated that any suitable imaging system may be selected by one of ordinary skill in the art.

Figure 15:
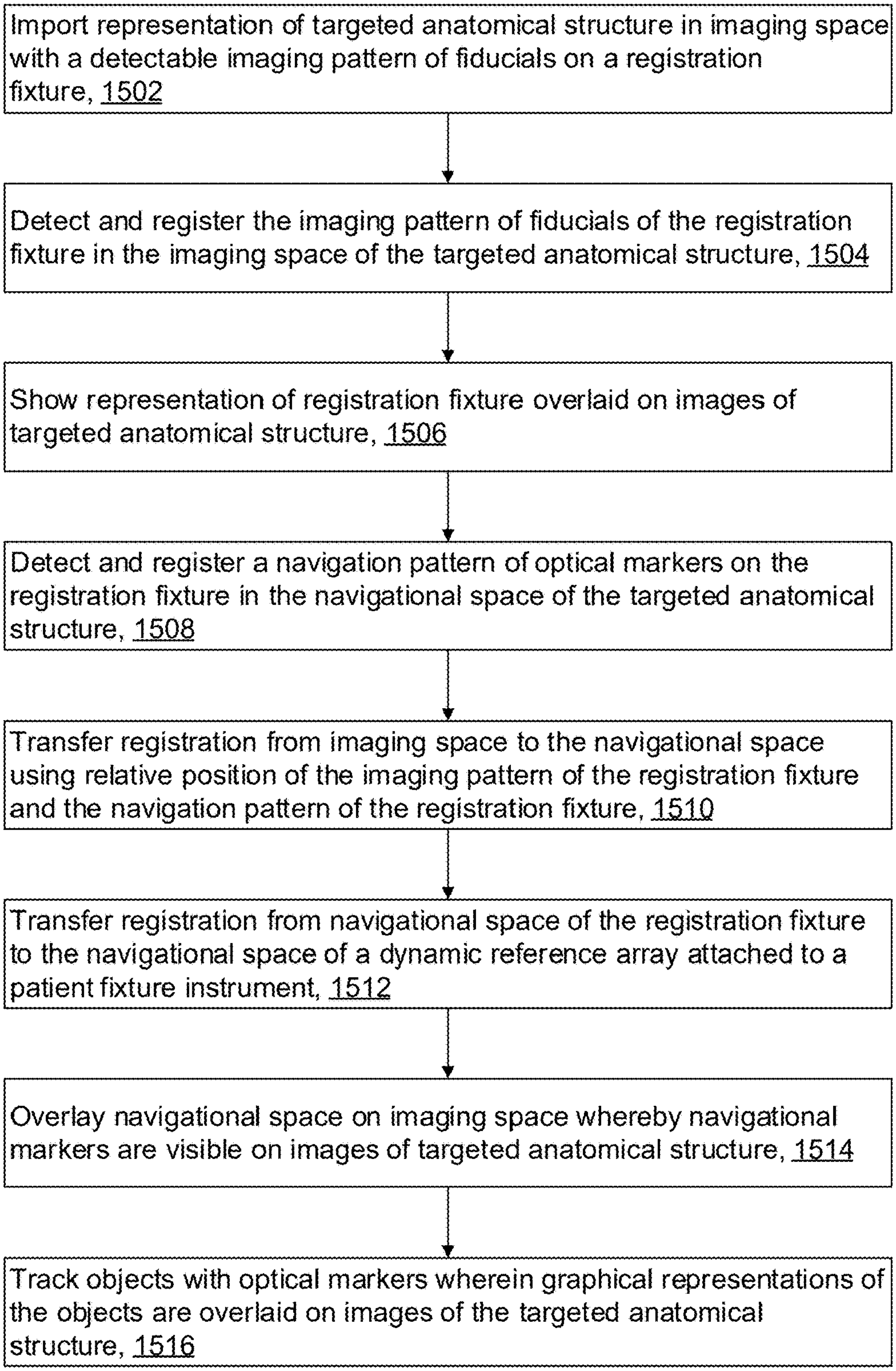
FIG. 15 illustrates a flow chart depicting a method of patient registration using a registration fixture and dynamic reference base, in accordance with embodiments of the disclosure.

FIG. 15 provides an exemplary method 1500 for registration using a registration fixture as described herein. Method 1500 begins at step 1502 wherein a graphical representation (or image(s)) of the targeted anatomical structure) may be imported into the robotic system, for example surgical planning computer 610. The graphical representation may be three dimensional CT or a fluoroscope scan of the targeted anatomical structure of the patient which includes a registration fixture and a detectable imaging pattern of fiducials. Registration fixtures for patient registration are described in further detail in U.S. Pat. No. 11,253,256, the entirety of which is hereby incorporated by reference as though fully set forth herein. At step 1504, an imaging pattern of fiducials is detected and registered in the imaging space and stored in computer 610. Optionally, at this time at step 1506, a graphical representation of the registration fixture may be overlaid on the images of the targeted anatomical structure. At step 1508, a navigational pattern of the registration fixture is detected and registered by recognizing markers. The markers may be optical markers that are recognized in the navigation space through infrared light by tracking subsystem 532 via position sensor 540. Thus, the location, orientation, and other information of the targeted anatomical structure is registered in the navigation space. Therefore, the registration fixture may be recognized in both the image space through the use of fiducials and the navigation space through the use of markers. At step 1510, the registration of the registration fixture in the image space is transferred to the navigation space. This transferal is done, for example, by using the relative position of the imaging pattern of fiducials compared to the position of the navigation pattern of markers. At step 1512, registration of the navigation space of the registration fixture (having been registered with the image space) is further transferred to the navigation space of the dynamic reference base, e.g., registration array, attached to patient fixture instrument. Thus, the registration fixture may be removed and the dynamic reference base may be used to track the targeted anatomical structure in both the navigation and image space because the navigation space is associated with the image space. At steps 1514 and 1516, the navigation space may be overlaid on the image space and objects with markers visible in the navigation space (for example, surgical instruments with optical markers). The objects may be tracked through graphical representations of, e.g., the surgical instrument on the images of the targeted anatomical structure.

Figure 16:
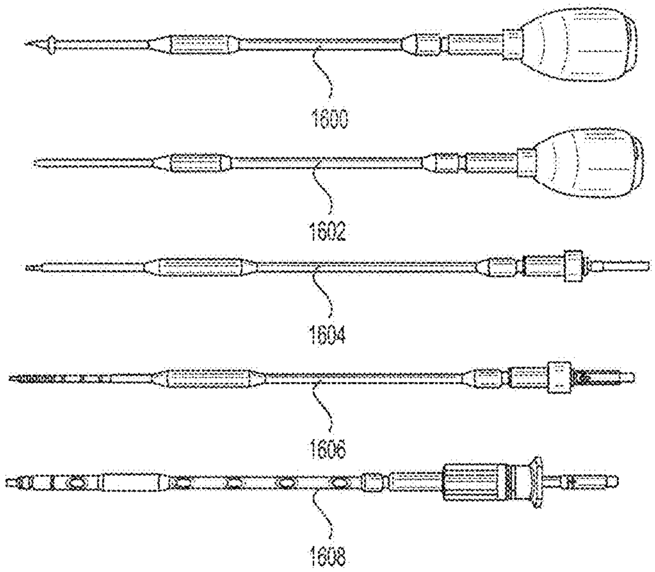
FIG. 16 illustrates a plurality of navigated surgical instruments, in accordance with embodiments of the disclosure.

As discussed herein, the robotic navigation computer system is configured to use one or more navigated surgical instruments during a surgical procedure. The navigated surgical instruments may be used, for example, to insert one or more patient attachment instruments (e.g., bone screws) into the patient. The navigated surgical instruments may include drills, awls, probes, taps, drivers, or combinations of these surgical instruments. FIG. 16 illustrates some embodiments of the navigated instruments, including an awl 1600, a probe 1602, a drill 1604, a tap 1606, and a driver 1608.

To navigate the surgical instrument, a DRB such as, e.g., an array may be coupled with the surgical instrument. The array includes a plurality of posts for attaching reflective markers arranged in a distinct marker pattern. The navigated surgical instruments are assembled to a corresponding instrument array, such that the distinct marker pattern identifies the corresponding navigated surgical instrument. The array may include a surface etched with a specific instrument type, e.g. "AWL", "PROBE", "DRILL", "TAP", "DRIVER". Each array may further include a verification divot used for instrument verification.

Figure 17:
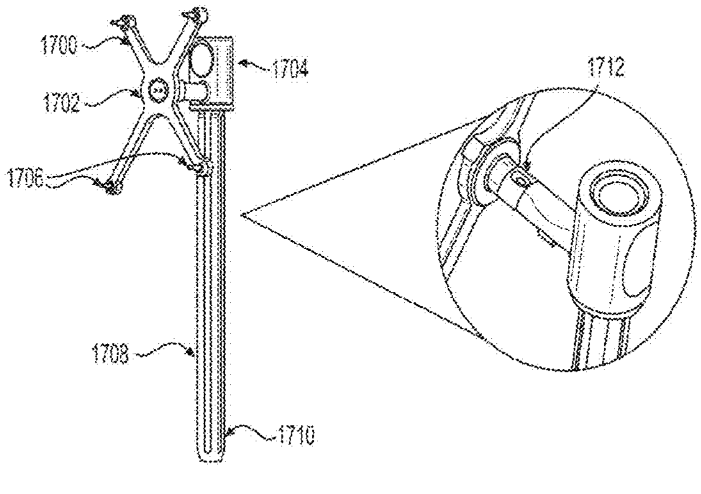
FIG. 17 illustrates an array, in accordance with embodiments of the disclosure.
Figure 18:
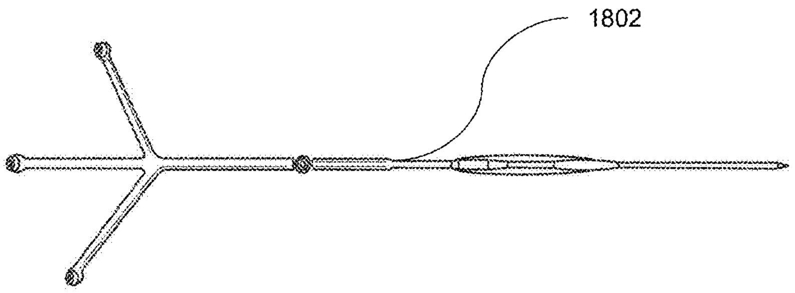
FIG. 18 illustrates a verification probe, in accordance with embodiments of the disclosure.

FIG. 17 illustrates an array 1700 according to some embodiments of the disclosure. As shown, the array 1700 includes a release button 1702, a handgrip 1704, a marker post 1706, an array sleeve 1708, an array support 1710, and a verification divot 1712 disposed between the array 1700 and the handgrip 1704. FIG. 18 illustrates a verification probe 1802 according to some embodiments. As shown, the verification probe 1802 includes a built-in array with posts for the reflective markers, which may be used to verify each instrument before use. Each navigated surgical instrument and corresponding array is assembled prior to use. During the surgical procedure, a camera (e.g., camera 904) recognizes the distinct array pattern associated with the corresponding navigated surgical instrument, which enables the robotic system to navigate the surgical instrument based on the location and orientation of the distinct array pattern.

The robotic system moreover includes one or more patient attachment instruments which are secured to the patient anatomy, depending on the specific surgical procedure or preference, and are available in various configurations. The patient attachment instruments may be secured to a variety of anatomical sites/features of the patient anatomy such as, e.g., vertebrae. The specific anatomical site to secure the patient attachment instrument depends, at least in part, on the specific type of patient attachment instrument being used and requirements of the surgical procedure based on medical images of the patient anatomy. To ensure navigation and guidance accuracy, the patient attachment instrument(s) must be safely and rigidly secured to the patient. If secure attachment is not maintained during the procedure then surveillance markers may demonstrate excessive movement, which requires the surgeon to re-position the patient attachment instrument and re-register the patient to the medical images.

Figure 19:
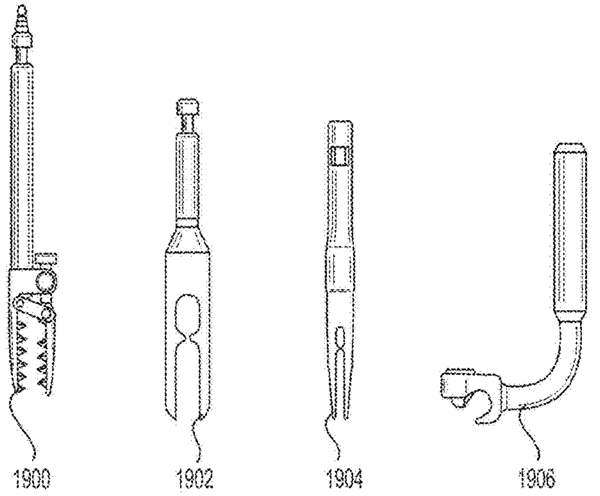
FIG. 19 illustrates a plurality of patient attachment instruments, in accordance with embodiments of the disclosure.

FIG. 19 illustrates several non-limiting examples of patient attachment instruments discussed herein. As shown, the patient attachment instruments may include a bone clamp 1900 with surveillance marker, a quattro spike 1902, a low profile quattro spike 1904, and/or a rod attachment 1906. The bone clamp 1900 is configured to be clamped onto any rigid bony structure of the patient anatomy that can be safely and securely clamped. For example, the bone clamp 1900 may be configured to be clamped onto one or more anatomical sites, including the spinous process, iliac crest, long bone, or any other rigid bone structure. The quattro spike 1902 and low profile quattro spike 1904 (hereinafter, "spikes 1902, 1904") may each be configured for insertion into a rigid bone structure of patient anatomy such as, e.g., rigid bone of the iliac crest and/or long bone. The spikes 1902, 1904 may be inserted into the rigid bone structure and blunt force is gently applied to securely fix the respective spikes 1902, 1904 to the patient anatomy. For example, the spikes 1902, 1904 may be inserted into a pilot hole formed via an awl within a vertebra, and a mallet is used to gently strike the spikes 1902, 1904 for fixation to the vertebra. The rod attachment 1906 is configured to couple with a spinal rod. For example, a spinal rod having a diameter in a range between approximately 4.5 mm and 6.35 mm, may be fixated to the patient anatomy. The rod attachment 1906 may engage a portion of the spinal rod, and be securely affixed to the spinal rod by tightening a set screw. Although four patient attachment instruments are shown, it should be understood that other patient attachment instruments known in the field of spinal procedures may alternatively or additionally be used and are contemplated within the scope of this disclosure.

ICT Fixtures

Surgical navigation often includes registration of fluoroscopic x-ray images to an optical tracking system, which enables robotic control/navigation and/or surgical planning. Prior to or during a surgical procedure, certain registration procedures may be conducted in order to track objects and patient anatomy both in a navigation space and an image space. In some embodiments, pre-operative imaging may be used to identify the patient anatomy to be targeted in the surgical procedure. If desired by the surgeon, a physical coordinate system may have coordinate axes anchored to specific anatomical landmarks such as, e.g., the anterior commissure (AC) and posterior commissure (PC) for neurosurgery procedures. In some implementations, multiple pre-operative medical images may be co-registered, such that it is possible to transform coordinates of any given point on the patient anatomy to the corresponding point on all other pre-operative exam images. For example, the ExcelsiusGPS® system is configured for planning placement of screws, positioning the robot, and/or navigating tools based on two or more registered fluoroscopic x-ray images. Moreover, the ExcelsiusGPS® system may register the fluoroscopic x-ray images (e.g., medical images) to a pre-operative CT scan. Accurate registration of fluoroscopic x-ray images is essential to the success of the surgical procedure.

As discussed herein, the patient registration process includes a dynamic reference base (DRB) such as, e.g., the DRB 1100 (FIG. 11), coupled with an intra-operative computer tomography (ICT) registration fixture which allows for any ICT image to be used with software applications of the robotic system. The ICT registration fixture is placed onto a patient attachment instrument such as, e.g., by clamping a compression clamp onto the instrument, thereby allowing the ICT registration fixture to hover over the patient anatomy during the surgical procedure. As described herein, an intra-operative scan (e.g., CT scan) of the patient anatomy, with the ICT registration fixture in the field of view, is used to register the patient anatomy to the DRB 1100 based on the location of fiducials which are detected automatically during the scan. For example, an intra-operative scan using the medical imaging system 1304 (FIGS. 13 and 14) to register the patient anatomy to the DRB 1100 based on the position of radiopaque materials disposed within, or otherwise coupled to, the ICT registration fixture which is in the field of view during the intra-operative scan.

Reflective markers 1108 on the DRB are tracked via one or more optical sensors (e.g., camera) throughout the surgical procedure. Because the DRB 1100 and ICT registration fixture are fixed relative to each other, registration can be complete by determining the location and orientation of the ICT registration fixture (e.g., from medical images) and the position of the reflective markers 1108, which may be used to determine the physical location of the patient anatomy thereby completing patient registration. Once registration is transferred to the DRB 1100, the ICT registration fixture is removed to provide access to the surgical site and continue to one or more subsequent operations in the surgical procedure.

The ICT registration fixture moreover includes one or more calibration phantoms as discussed herein. The term "calibration phantom" as used herein refers to an object or structure which is used as a reference standard to calibrate, validate, or otherwise assess the quality of a medical imaging device such as, e.g., a CT scanner. The calibration phantom mimics the properties of human tissue, providing a known and consistent set of measurements which allow for accurate quantification of bone mineral density (BMD) of patient anatomy. For example, the calibration phantom may include a compartment having a material disposed therein which, when captured via fluoroscopic images, simulates BMD at a known value. Scanning the calibration phantom using similar imaging parameters as scans of the patient anatomy allows the robotic system to establish a relationship between the Hounsfield Unit (HU) values of the calibration phantom and corresponding simulated BMD values. The calibration phantom therefore calibrates the medical imaging device by simulating known BMD values, which correspond to an expected HU value in the fluoroscopic shots, enabling calibration via any discrepancy in a measured HU value of the calibration phantom in the fluoroscopic shots relative to the expected HU value of simulated BMD. In some implementations, the calibration phantom includes a plurality of materials having a plurality of known, simulated BMD values. The plurality of materials may each have a different known, simulated BMD value. For example, the calibration phantom may include a first material having a first simulated BMD and a second material having a second simulated BMD that is different from the first simulated BMD. The medical imaging device therefore may derive the relationship between HU and BMD values in fluoroscopic images based on the calibration phantom and known BMD values thereof, and in turn determine the BMD value of the patient anatomy based on the derived relationship. The surgeon may use derived BMD measurements, for example, to identify regions of low BMD that may affect the success of implant fixation and/or fusion.

Figure 20:
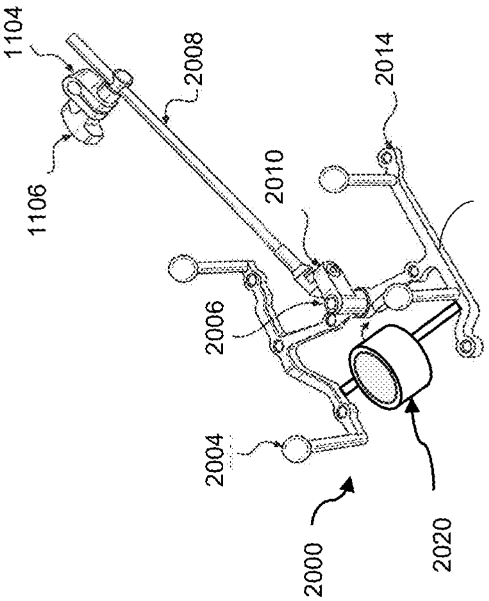
FIG. 20 illustrates an intra-operative computer tomography (ICT) registration fixture and dynamic reference base, in accordance with embodiments of the disclosure.

FIG. 20 illustrates an ICT registration fixture 2000 according to some embodiments of the disclosure.

Figure 21:
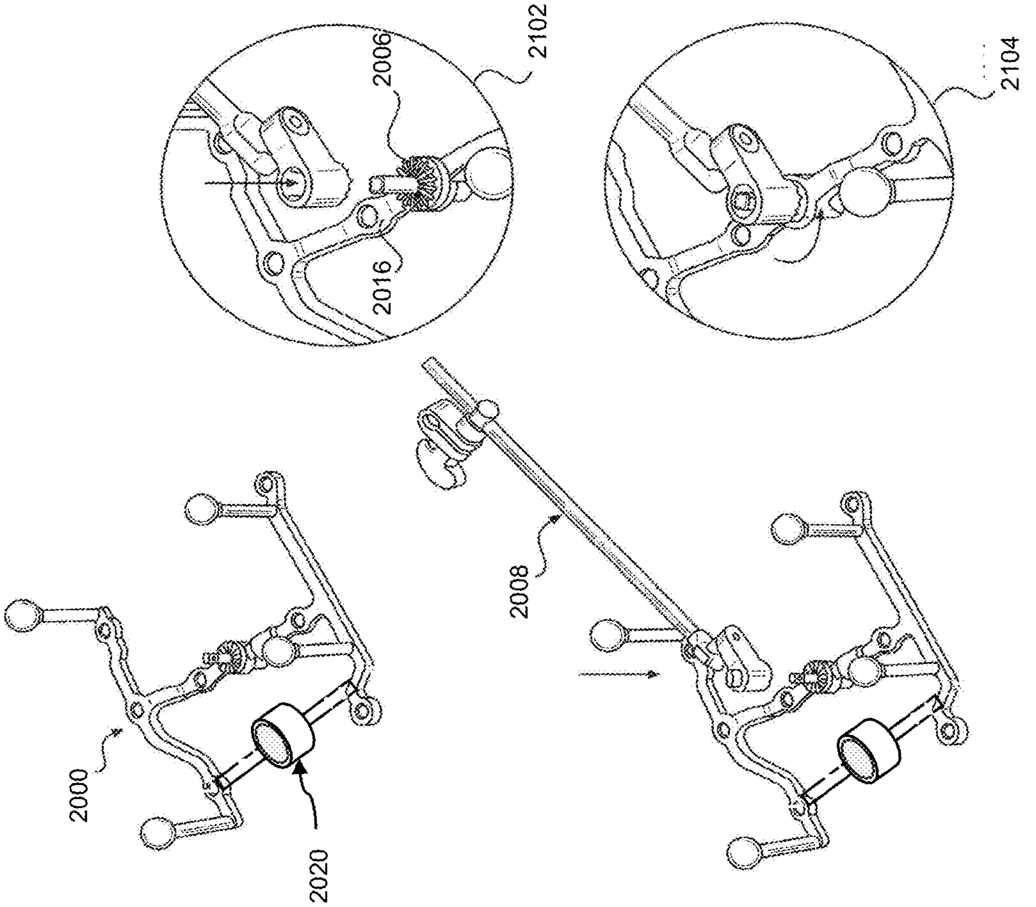
FIG. 21 illustrates assembling the ICT registration fixture and dynamic reference base of FIG. 20, in accordance with embodiments of the disclosure.

As shown, the ICT registration fixture 2000 includes a frame 2002 having one or more markers 2014 disposed therein. The frame 2002 may include a strong, radiolucent material such as, e.g., a biocompatible plastic, metal, or combination of materials. The registration fixture 2000 further includes a plurality of reflective markers 2004 disposed thereon. As further shown, the registration fixture 2000 includes a starburst connection 2006 disposed on the frame 2002 for coupling a pivoting arm 2008 to the frame 2002 via a gear tooth joint 2010. The pivoting arm 2008 is configured to fixedly couple with the compression clamp 1104, and thereby to secure the registration fixture 2000 to the DRB 1100 in a known configuration. FIG. 21 illustrates attaching the frame 2002 to the pivoting arm 2008, which is engaged with the compression clamp 1104. Referring to the enlarged view 2102 of the pivoting arm 2008 positioned over the starburst connection 2006, a user may push the lock post 2016 of the frame 2002 from the bottom and rotate the arm 90° until the pin in the lock post 2016 is seated to secure the fixture. Enlarged view 2104 shows the pivoting arm 2008 attached and rotated to become secured to form the registration fixture 2000.

As further shown in FIG. 20, the registration fixture 2000 includes one or more markers 2014 that include a radiopaque material which, when imaged via CT scanning, provides sufficient contrast to be distinguishable in the resulting CT scan image yet limiting distortion or scatter. Markers 2014 may include, e.g., titanium ball bearings as shown in FIG. 20. For example, the registration fixture 2000 may include seven (7) markers 2014 (e.g., titanium ball bearings) disposed in seven (7) corresponding apertures in the frame 2002. However, the registration fixture 2000 may alternatively include a different quantity of markers 2014 disposed therein such as e.g., four, five, six, eight, etc., markers 2014 disposed within corresponding apertures in the frame 2002. The markers 2014 may be pressed into the apertures and fixedly attached to the frame 2002 such as, e.g., via compression fit, snap-fit, etc. Positioning each marker 2014 centrally within the respective apertures may cause any distortion or scatter that is present in the CT image to appear symmetrically disposed around each marker 2014. Any distortion or scatter may be filtered, or substantially filtered, from the CT image based on the known, central position of each marker 2014 relative to the frame 2002. In some implementations, the markers 2014 are fixedly attached to the frame 2002 via adhesive or welding materials. However, the presence of these additional bonding materials may further distort or scatter the CT image, and their use may accordingly be limited.

As shown in FIG. 20, the registration fixture 2000 may further include a calibration phantom 2020. The calibration phantom 2020 may include any material, or combination of materials, having a known BMD or simulated BMD value and substantially similar x-ray attenuation properties as human bone and tissue. In some implementations, the calibration phantom 2020 includes inserts or compartments made from material such as, e.g., hydroxyapatite, plastic, polymers, or other materials of known BMD or simulated BMD value. As x-rays pass through different types of tissue, the x-rays undergo attenuation and beam hardening. The calibration phantom 2020 may be used to create a calibration curve which accounts for the effects of tissue composition and/or x-ray beam hardening. In some implementations, the calibration phantom 2020 may be encapsulated or otherwise protected, such that an external environment does not alter or otherwise affect the calibrated phantom 2020 or calibration thereof.

Figure 22:
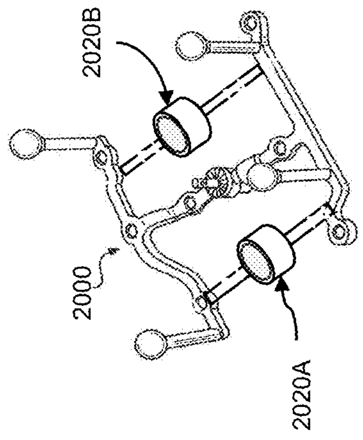
FIG. 22 illustrates an ICT registration fixture according to another embodiment of the disclosure.

In some implementations, the ICT registration fixture includes two or more calibration phantoms. FIG. 22 illustrates an ICT registration fixture 2200 that includes a first calibration phantom 2020A and a second calibration phantom 2020B. The first calibration phantom 2020A has a first material disposed therein, and the second calibration phantom 2020B has a second material disposed therein. The first and second materials each simulate known BMD values to use as reference standards for the medical imaging device to derive the relationship between HU and BMD from fluoroscopic images.

Figure 23:
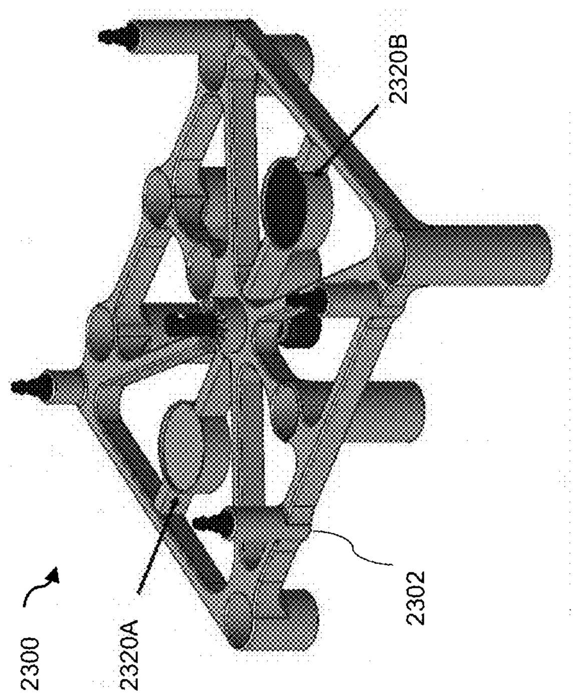
FIG. 23 illustrates an ICT registration fixture according to another embodiment of the disclosure.

The calibration phantoms described herein can be embedded within any ICT registration fixture. For example, FIG. 23 illustrates an ICT registration fixture 2300 according to another embodiment of the disclosure. As shown, the ICT registration fixture 2300 includes a frame 2302 having a first calibration phantom 2320A and a second calibration phantom 2320B embedded therein. The calibration phantoms 2320A, 2320B operate the same way as described with reference to FIGS. 20-22, the details of which are omitted for brevity.

Figure 24:
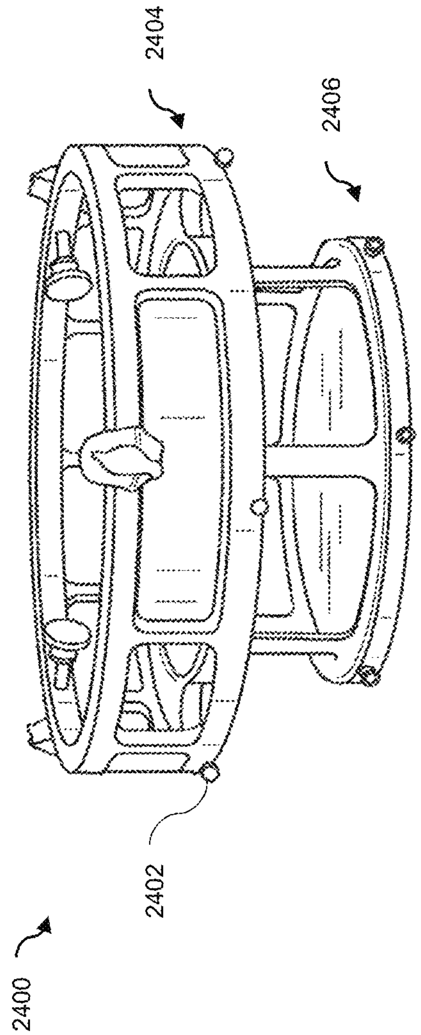
FIG. 24 illustrates a fluoroscopy registration fixture, in accordance with embodiments of the disclosure.

FIG. 24 illustrates a fluoroscopy registration fixture 2400 which allows for any intra-operative fluoroscopic image to be used with software applications of the robotic system. The registration fixture 2400 is configured to register fluoroscopic images (e.g., “fluoro shots”) to an optical tracking system. The registration fixture 2400 is attached to an image intensifier of a fluoroscope using one or more integrated clamps. The fluoroscope and registration fixture 2400 may be draped in a manner similar to the drape shown in FIG. 7, and reflective markers are placed on the registration fixture, outside of the drape. The registration fixture 2400 may be positioned such that the reflective markers are seen by the camera in all intended fluoroscope positions such as, e.g., anterior-posterior, lateral, medial, etc.

The registration fixture 2400 may include optical tracking markers such as, e.g., reflective spheres and/or light-emitting diodes, which are used by the optical tracking system to track the position of the registration fixture 2400 relative to the patient anatomy. The registration fixture 2400 further includes a plurality of radiopaque fiducials such as, e.g., multiple arrays of metal spheres (BBs) dispersed/embedded in at least two planes which create a pattern of x-ray shadows on fluoroscopic images. In the embodiment shown in FIG. 24, the registration fixture 2400 includes six (6) optical tracking markers 2402, and a first BB plane 2404 and a second BB plane 2406 which each include BBs disposed therein. The BBs are not visible, but are embedded in a radiolucent material including respective BB planes, such that each BB blocks x-rays to provide a respective shadow in a fluoroscopic image generated using the x-ray detector. The positions of the optical tracking markers 2402 are captured by the optical tracking system (e.g., camera 904) at the time the fluoroscopic image is taken, allowing the location of the image plane of x-ray detector 2504 to be accurately tracked. From image processing, the shadows created by the BBs and cast on the image plane allow the location of the x-ray source 2502 to be accurately determined using the geometric constraints of a pinhole camera model as shown in FIG. 25 and discussed further herein below.

Figure 25:
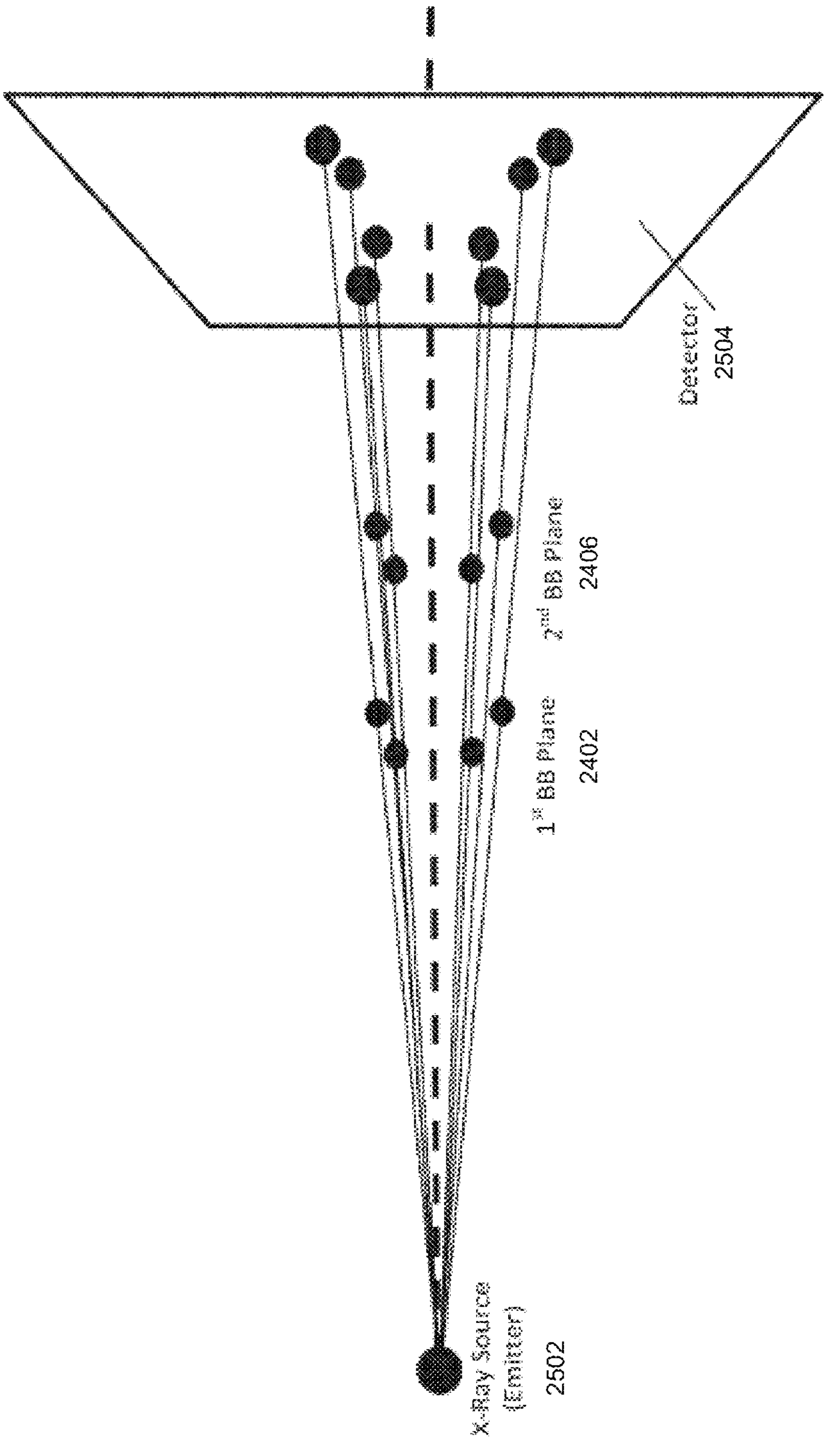
FIG. 25 illustrates a diagram of a pin hole camera, in accordance with embodiments of the disclosure.

FIG. 25 is a schematic diagram illustrating concepts of a pinhole camera model. As shown, x-rays from a point source (i.e., x-ray source 2502, also referred to as an x-ray emitter, an emitter, or a source) travel through tissue (between x-ray source 2502 and first BB plane 2404) until reaching the x-ray detector 2504 (i.e., image intensifier), where the fluoroscopic image is generated. If the spacing between BBs and BB planes 2404, 2406 is known, the pattern of x-ray shadows projected on the 2D image plane of the x-ray detector 2504 dictates where the x-ray source 2502 is located relative to the x-ray detector 2504. Knowing the location of the x-ray source 2502 and x-ray detector 2504 in camera space (e.g., of the optical tracking system), mathematical transformations may be used to move between the camera space and two 2D image planes from two fluoroscopic images. For example, if an object is in a known location in camera space, its projection's representation can be rendered onto each image plane exactly where the object's projections would appear as if a new pair of fluoroscopic images were taken from the same orientations. Conversely, if an object's projections are added to the two 2D image planes (like a projected screw image added to the surgical plan on anteroposterior (A-P) and lateral fluoroscopic images), the 3D location of the object in camera space can be determined.

Figure 26:
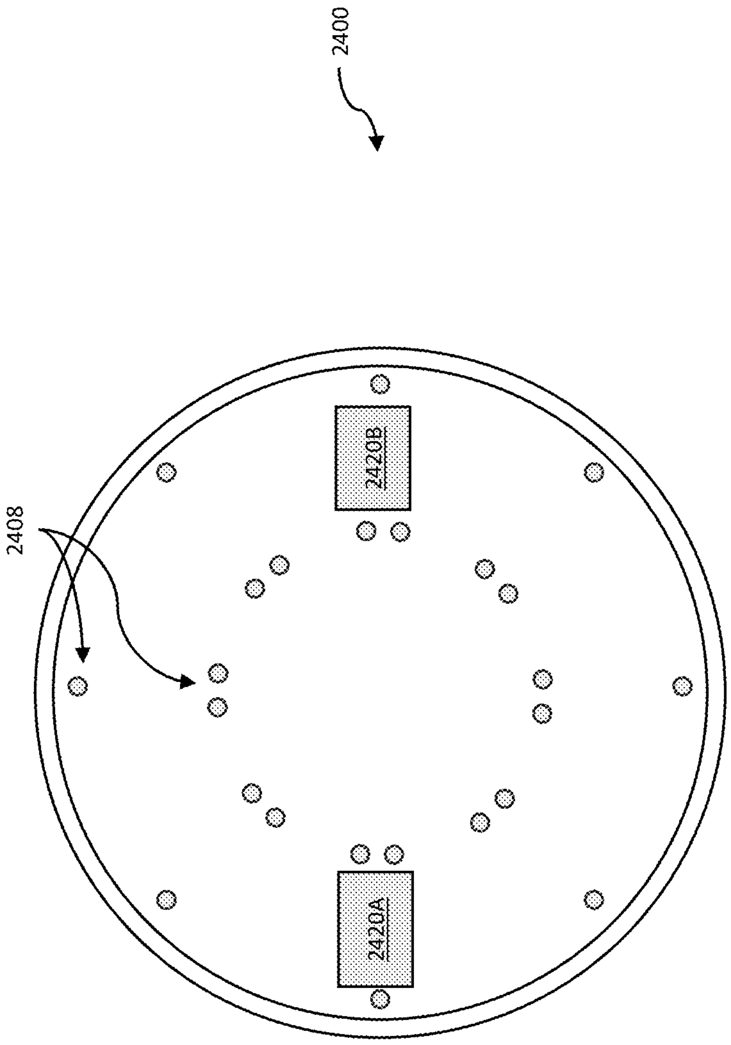
FIG. 26 illustrates a cross-section view of the fluoroscopy registration fixture of FIG. 24, in accordance with embodiments of the disclosure.

FIG. 26 illustrates a cross-section of the registration fixture 2400. As shown, the registration fixture 2400 may include a plurality of BBs 2408 configured to create shadows on the image plane. The registration fixture 2400 may further include a plurality of calibration phantoms 2420A, 2420B configured to simulate a plurality of BMD values in fluoroscopic images. The calibration phantoms 2420A, 2420B are configured to calibrate the medical imaging device based on the simulated BMD values, which correspond to known HU values in fluoroscopic images as discussed above regarding registration fixtures 2000, 2100 and 2200, the details of which are omitted herein for brevity.

Figure 29:
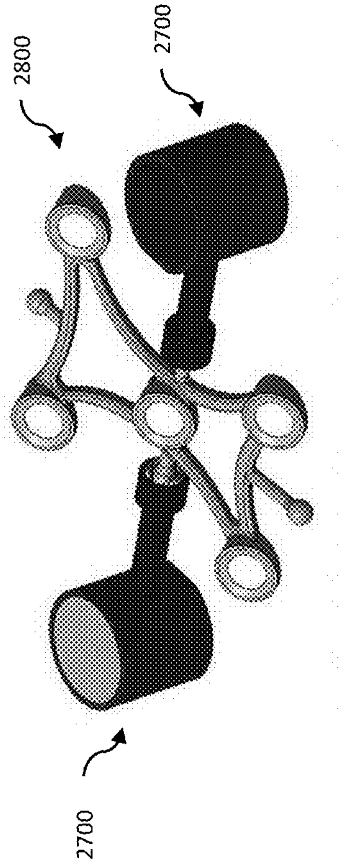
FIG. 29 illustrates an assembled perspective view of the modular calibration phantom of FIG. 27 and the ICT registration fixture of FIG. 28, in accordance with embodiments of the disclosure.
Figure 27:
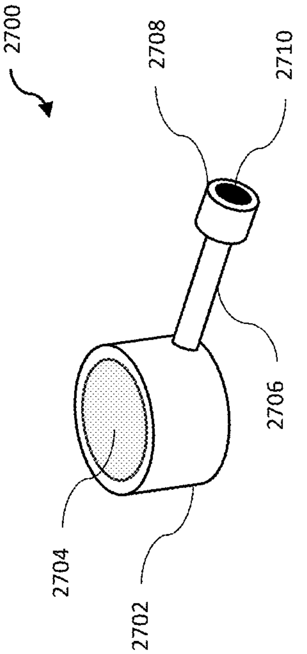
FIG. 27 illustrates a perspective view of a modular calibration phantom, in accordance with embodiments of the disclosure.
Figure 30:
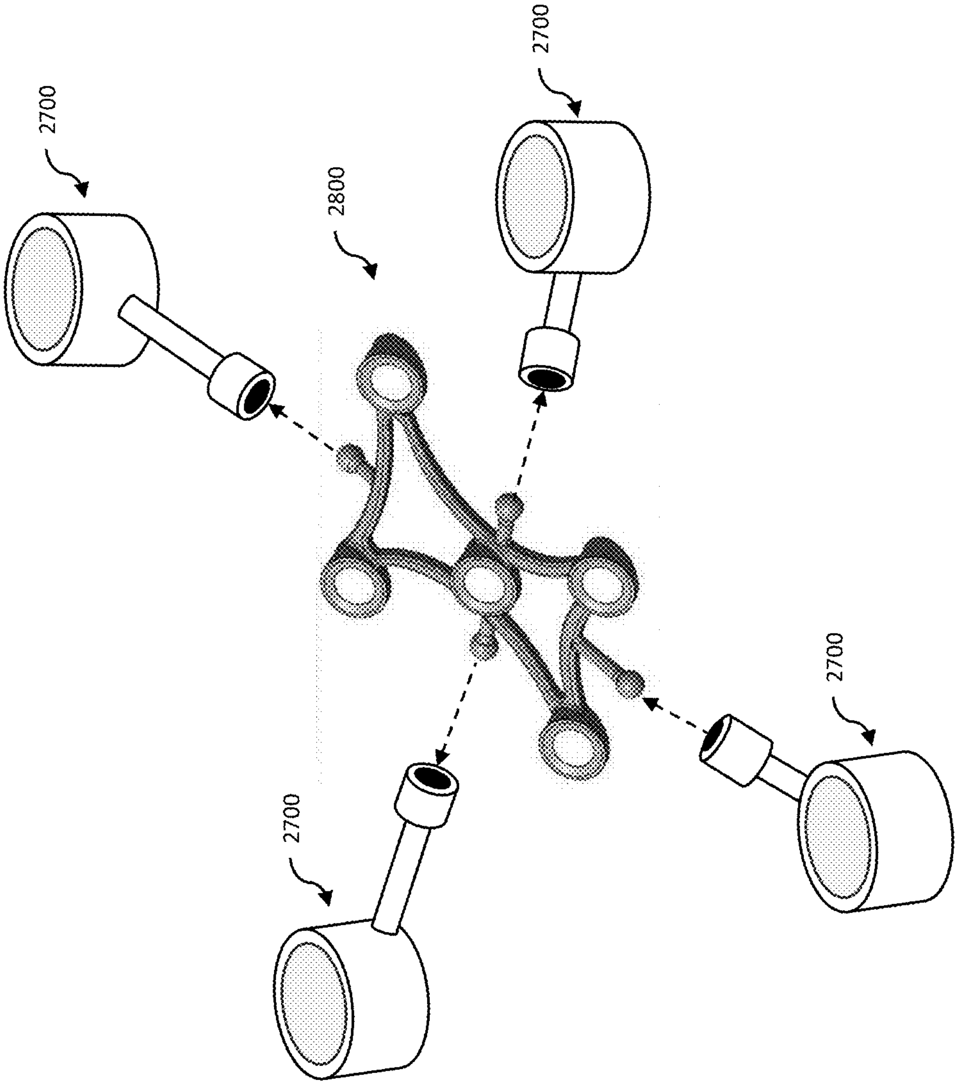
FIG. 30 illustrates an exploded perspective view of the modular calibration phantom of FIG. 27 and the ICT registration fixture of FIG. 28 according to another embodiment of the disclosure.

FIG. 27 illustrates a modular calibration phantom 2700 to simulate BMD values during patient registration of the patient anatomy, and thereby to calibrate the medical imaging device as discussed herein. As shown, the modular calibration phantom 2700 includes a compartment 2702 having at least one material 2704 disposed therein. The at least one material 2704 is configured to simulate at least one BMD value during an intra-operative scan, which corresponds to at least one known HU value in medical image output from the scan. Discrepancy between the at least one known HU value, and a measured HU value in the medical image, may be used to determine a relationship between actual BMD of patient anatomy and measured BMD of patient anatomy. In some implementations, the compartment 2702 includes two or more materials disposed therein, which simulate two or more distinct BMD values during the intra-operative scan corresponding to two or more distinct known HU values in medical images output from the scan. The modular calibration phantom 2700 may be shaped and dimensioned to couple with one or more registration fixtures and/or patient attachment fixtures such as, e.g., DRBs, ICT registration fixtures, fluoroscopic registration fixtures, bone clamps, quattro spikes, rod attachments, etc. As shown, the modular calibration phantom 2700 may include an engagement portion 2706 which extends away from the compartment 2702 toward an engagement end 2708 configured to engage at least one fixture described herein. In some implementations, the engagement portion 2706 includes a socket 2710 at the engagement end 2708, which is configured to receive a portion of the fixture therein such as, e.g., a ball extending from the fixture. For instance, the modular calibration phantom 2700 may be configured to engage an ICT registration fixture 2800 as shown in FIGS. 28-30.

Figure 28:
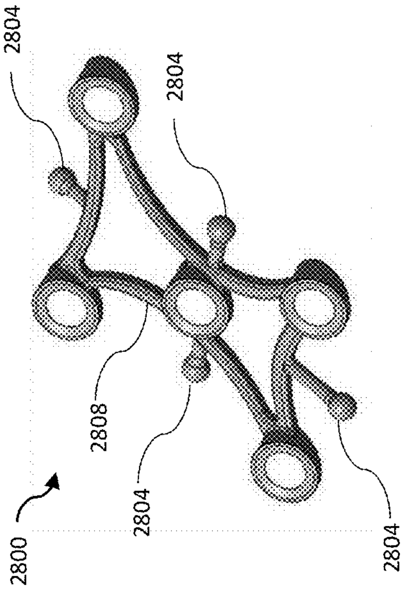
FIG. 28 illustrates a perspective view of an ICT registration fixture according to another embodiment, in accordance with embodiments of the disclosure.

FIG. 28 illustrates an ICT registration fixture 2800 according to another embodiment. As shown, the registration fixture 2800 includes a frame 2802 having a plurality of engagement portions 2804 disposed thereon. In the embodiment depicted, the registration fixture 2800 includes four (4) engagement portions 2804 radially extending away from the frame 2802. However, a different quantity of engagement portions 2804 such as e.g., two, three, five, six, seven, eight, etc., engagement portions 2804 may be disposed on the frame 2802, and the engagement portions 2804 may be arranged in a configuration differing from the one shown. As shown, each engagement portion 2804 of the plurality of engagement portions 2804 includes a ball configured to matingly engage a corresponding socket 2710 of the modular calibration phantom 2700. FIG. 29 illustrates an assembled perspective view of the registration fixture 2800 coupled with two modular calibration phantoms 2700 disposed on opposite sides of the frame. FIG. 30 illustrates an exploded perspective view of the registration fixture 2800 and four (4) calibration phantoms 2700.

Therefore, the modular calibration phantom 2700 may be coupled with existing registration fixtures or patient attachment fixtures, and thereby enable the respective fixture to calibrate BMD or simulated BMD for a medical imaging device.

One or more embodiments presented herein may allow for patient anatomy to be quickly and accurately registered to a fixed reference array regardless of the imaging system being used. This feature is in contrast, for example, to existing systems that use tracking cameras to track the position of a marker array on the imaging system at the time of the scan relative to a marker array on the patient in order to establish registration of the tracking coordinate system with the image coordinate system. Most imaging systems do not have tracking markers and lack calibration of the image field to allow such a method to work universally. As discussed herein, one or more embodiments may use locations of markers as detected from an image processing scan, which determine if the scan volume is readable by the system.

Moreover, one or more embodiments described herein allow a registration device to be positioned where desired, as the registration device includes its own tracking markers and will later be removed. This is in contrast to other methods in which a bone-mounted tracking array, containing both retroreflective spheres and an extension or feature with radiopaque markers, is used for registration and positioned relatively close to a tracking array, thereby having limited adjustability. Such a registration device could either inadvertently block the surgeon's access, obscure tracking markers, or require suboptimal positioning of the CT scanner to capture all the radiopaque spheres in the scan. One or more embodiments described herein may allow a registration device to be placed relatively further from a rigid tracking array, be easily adjustable to be close to the patient's skin, and be removed from the path of surgery after registration transfer to the tracking array.

Merge Fixtures

As discussed herein, patient registration involves correlating medical images of the patient anatomy (e.g., x-ray, CT) with the actual position of the patient anatomy during the surgical procedure, and contributes greatly to the efficacy of navigated and robotic surgical procedures. However, intra-operative fluoroscopy of the patient anatomy can sometimes be difficult due to, for example, low quality fluoroscopy images, artifacts in fluoroscopy images, and/or a deformity or size of the patient anatomy. In these scenarios, it may be necessary to repeat intra-operative fluoroscopy a multitude of times until adequate medical images are obtained for registration. This iterative process may increase radiation exposure to the patient and/or staff and may increase operating time of the surgical procedure. It would be advantageous to implement alternative techniques to perform patient registration that do not rely solely on crisp fluoroscopy images and/or do not require intra-operative fluoroscopy. Patient specific, fluoroscopy merge fixtures and related methods address these issues, among others, in the field of spinal surgical procedures.

With reference to FIGS. 31A-31F, a patient specific fluoroscopy merge fixture 3100 is illustrated according to an embodiment of the disclosure.

Figure 31D:
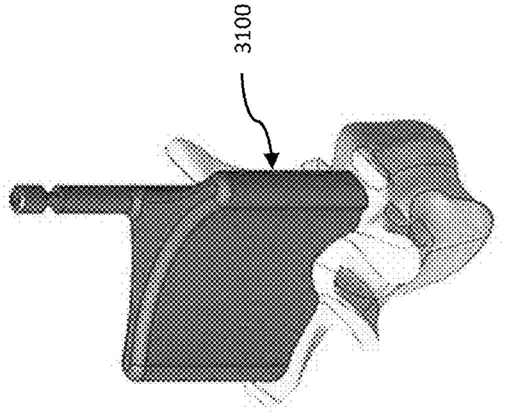
FIGS. 31A-31F illustrate various views of a merge fixture according to some embodiments of the disclosure.
Figure 31B:
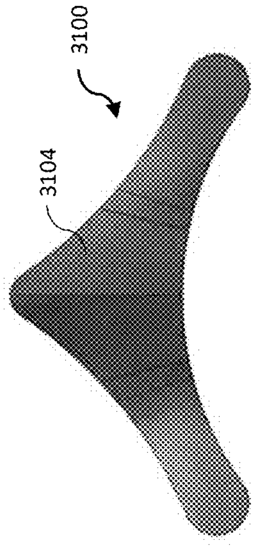
Figure 31C:
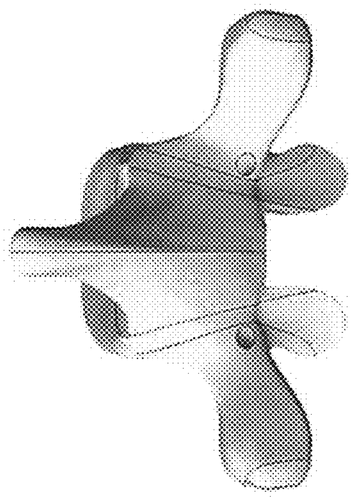
Figure 31A:
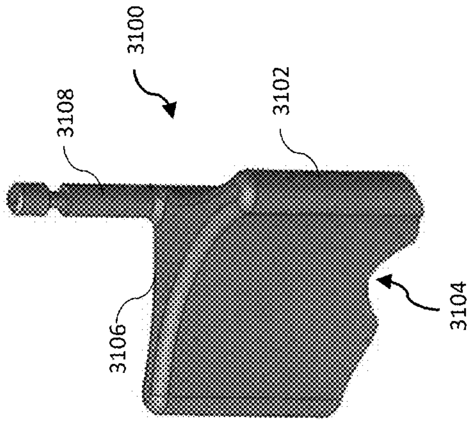

FIG. 31A shows the merge fixture 3100 including a body 3102 having at least one surface shaped and dimensioned to complement and engage an anatomical feature of the patient anatomy such as, e.g., the transverse process, lamina, facets, and/or spinous process of a vertebra or another anatomical feature of a patient. As shown, the body 3102 of the merge fixture 3100 includes a first surface 3104 shaped and dimensioned to engage a specific vertebra of the patient anatomy, and a second surface 3106 opposite the first surface 3104. For example, the first surface 3104 may be shaped and dimensioned to matingly engage the contour of the L4 vertebra of the patient anatomy. FIG. 31B shows the first surface 3104 of the body 3102, which is shaped and dimensioned to matingly engage the contour of the vertebra shown in FIG. 31C. The contour of the anatomical feature (e.g., specific vertebra) may be derived from 3D medical images of the patient anatomy captured by one or more medical imaging devices (e.g., FCT scan, MRI, etc.). Once the contour of the anatomical feature is known, a 3D model of the merge fixture 3100 can be made to fixedly engage the anatomical feature in a known orientation and location on the patient anatomy, as shown in FIG. 31D.

The 3D model of the merge fixture 3100 may include any 3D computer readable file capable of providing instructions to one or more devices (e.g., 3D printers) capable of rendering and/or manufacturing the merge fixture 3100 based on the 3D model. For example, the 3D model may include a Standard Tessellation Language (STL) file, which may be used by an additive manufacturing device to create the merge fixture 3100 layer-by-layer. The merge fixture 3100 can be made of any radiolucent material or combinations of radiolucent materials such as, e.g., metal, plastic, etc. The merge fixture 3100 moreover includes an engagement feature 3108 which extends from the body 3102 and is configured to matingly engage a DRB as described herein.

Figure 31E:
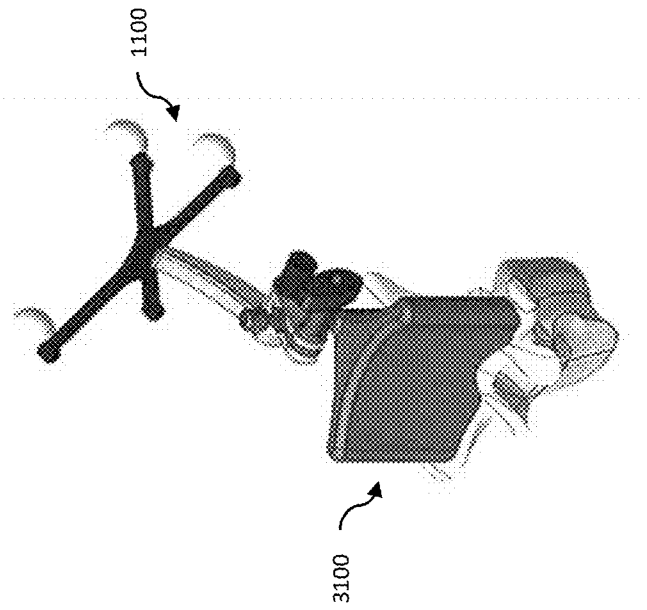
Figure 31F:
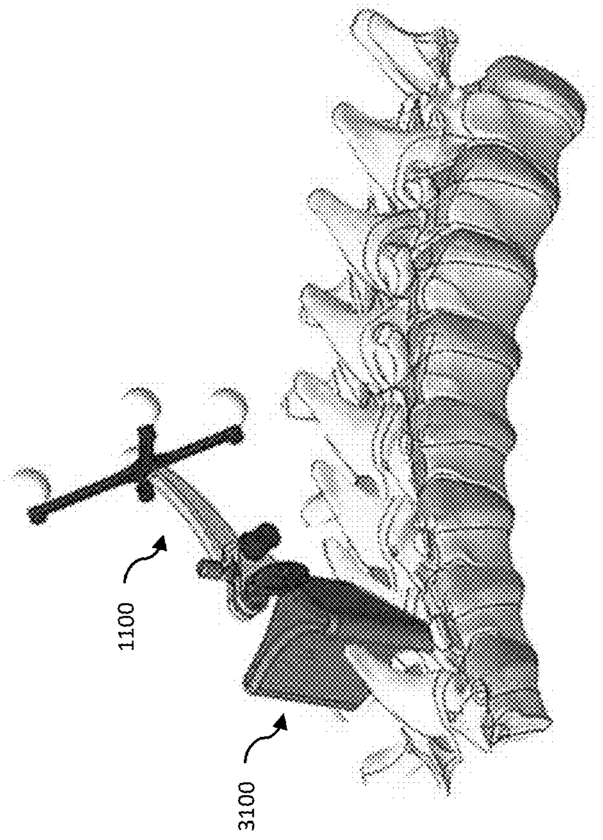

As shown in FIGS. 31E and 31F, the engagement feature 3108 may extend superiorly from the second surface 3106 to engage the compression clamp 1104 of the DRB 1100, which is configured to receive the engagement feature 3108 of the merge fixture 3100 therein. The DRB 1100 is coupled to the merge fixture 3100 in a known location and orientation. After sterilization, the assembly including the DRB 1100 and merge fixture 3100 are affixed to the anatomical feature of the patient anatomy.

During the surgical procedure, one or more optical sensors (e.g., the camera 904) may transmit electromagnetic signals (e.g., infrared light) toward the DRB 1100, which in turn reflects electromagnetic signals via the reflective markers 1108 corresponding to the location and orientation of the DRB 1100. These reflections enable the robotic system to triangulate the position and orientation of the DRB 1100 relative to the optical sensor (e.g., camera 904) within a coordinate system. The position and orientation of the merge fixture 3100 may be derived from the triangulated position and orientation of the DRB 1100, which is affixed to the merge fixture 3100 via the clamp 1104 (FIGS. 11, 20) in a known position and orientation. The DRB 1100 therefore may be useful to track the position of the merge fixture 3100 during a surgical procedure without intra-operative fluoroscopic imaging. Because the merge fixture 3100 can only be affixed in a specific location and orientation relative to the patient anatomy, the robotic system is able to determine a specific location and orientation of the spine during the surgical procedure, and thereby to complete patient registration. The robotic system is further configured to receive user input during the surgical procedure, which indicates that the merge fixture 3100 is affixed to the vertebra in the specific location and orientation relative to the patient anatomy. In response to the user input, the robotic system may determine the specific location and orientation of the spine based on the reflected signals and pre-determined location and orientation of the merge fixture 3100. Therefore, the merge fixture 3100 enables patient registration without the need for any intra-operative fluoroscopy. This mitigates radiation exposure to the patient and/or medical professionals during the surgical procedure.

Figure 32:
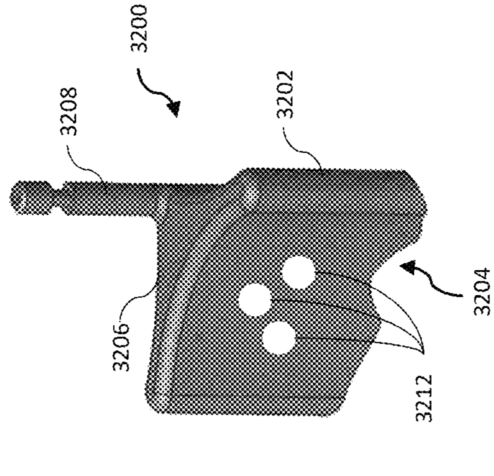
FIG. 32 illustrates a merge fixture according to another embodiment of the disclosure.

In some implementations, the merge fixture may further include one or more fiducials embedded therein. Referring now to FIG. 32, a merge fixture 3200 having one or more fiducials therein is illustrated according to some embodiments. As shown, the merge fixture 3200 includes a body 3202 having a first surface 3204 opposite a second surface 3206, and an engagement portion 3208 that extends superiorly from the second surface 3206 to engage a dynamic reference base such as, e.g., the DRB 1100. Although the merge fixture 3200 has a complementary shape and dimensions relative to an anatomical feature, soft tissue of the patient anatomy (e.g., muscles, tendons, ligaments) may interfere with placing the merge fixture 3200 in the predetermined position and orientation relative to the patient anatomy with sufficient accuracy to complete patient registration. In order to account for the discrepancy in the merge fixture 3200 position and orientation due to soft tissue, intra-operative fluoroscopy images can be taken with the merge fixture 3200 in the field of view to determine the actual position and orientation of the merge fixture 3200 relative to the patient anatomy.

As further shown in FIG. 32, the merge fixture 3200 includes a plurality of BBs 3212 embedded within the body 3202 in a specific and known arrangement, such that the position of each BB 3212 within the body 3202 relative to other BBs 3212 is known. The BBs 3212 can be made of one or more radiopaque materials such as, e.g., stainless steel. The merge fixture 3200 may include a plurality of pockets disposed within the body 3202 configured to securely retain one or more respective BBs of the plurality of BBs 3212 therein. In some implementations, the merge fixture 3200 can be formed via additive manufacturing (e.g., 3D printing), such that the body 3202 is manufactured to include the plurality of pockets at known positions therein. Each pocket retains at least one respective BB 3212 therein, such that the plurality of BBs 3212 are in a specific known arrangement unique to the merge fixture 3200, such that no two merge fixtures 3200 have the same configuration of radiopaque material in the robotic system during the surgical procedure. The robotic system is configured to analyze fluoroscopy images and identify the pattern of BBs 3212 embedded within the merge fixture 3200. The robotic system may derive location and orientation of the patient anatomy based on the pattern of BBs 3212 displayed on the intra-operative fluoroscopy images. Therefore, the pattern of BBs 3212 enables the robotic system to determine any shift or discrepancy between the pre-determined position and the actual position of the merge fixture 3200 relative to the patient anatomy, thereby completing patient registration.

Figure 33:
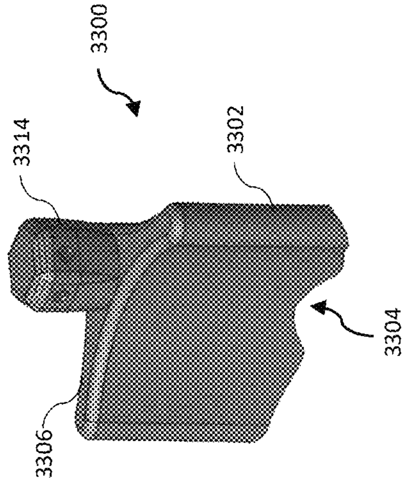
FIG. 33 illustrates a merge fixture according to another embodiment of the disclosure.

FIG. 33 illustrates a merge fixture 3300 according to another embodiment of the disclosure. The merge fixture 3300 includes a body 3302 having a first surface 3304 opposite a second surface 3306. The first surface 3304 is shaped and dimensioned to complement and engage an anatomical feature (e.g., vertebra) of the patient anatomy. The merge fixture 3300 further includes a transmitter 3314 disposed on the second surface 3306. The transmitter 3314 is configured to transmit electromagnetic signals such as, e.g., infrared light, from the merge fixture 3300 and to a receiver configured to receive electromagnetic signals such as, e.g., the camera 904 (FIG. 9). The transmission of electromagnetic signals enable the robotic system to triangulate the position of the merge fixture 3300 within a coordinate system. Since the merge fixture 3300 can only engage the anatomical location at a specific location and orientation relative to the patient anatomy, the triangulated position enables the robotic system to determine the position and orientation of the anatomical feature. In the present embodiment, the transmitter includes an active light emitting diode (LED) which extends superiorly from the body 3302 of the merge fixture 3300, and away from the patient anatomy during the surgical procedure. However, it should be understood that alternative transmitter devices, or combinations of devices, may alternatively or additionally be used to triangulate the position of the merge fixture 3300 during the surgical procedure. In alternative embodiments, for example, one or more transmitters may be embedded within the body 3102 of the merge fixture 3300 in a known position. The transmitter 3314 therefore may be useful to track the position of the merge fixture 3300 during a surgical procedure without intra-operative fluoroscopic imaging, which in turn may be useful to derive the position of the anatomical feature coupled with the merge fixture 3300.

Figure 34:
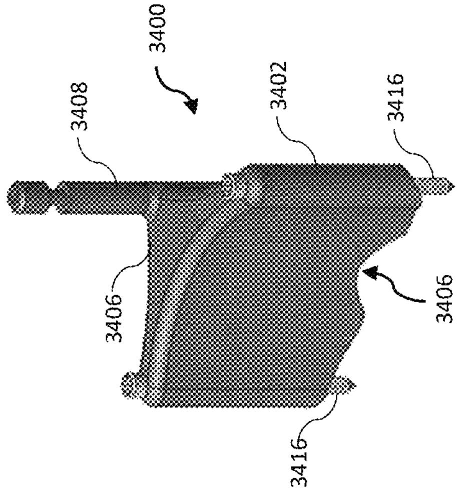
FIG. 34 illustrates a merge fixture according to another embodiment of the disclosure.

FIG. 34 illustrates a merge fixture 3400 according to another embodiment of the disclosure. The merge fixture 3400 includes a body 3402 having a first surface 3404 opposite a second surface 3406. The first surface 3404 is shaped and dimensioned to complement and engage an anatomical feature (e.g., vertebra) of the patient anatomy. An engagement portion 3408 extends away from the second surface 3406 and is configured to engage a dynamic reference base such as, e.g., DRB 1100. The body 3402 further includes a pair of channels extending through the body 3402 between the first surface 3402 and the second surface 3406. The pair of channels are shaped and dimensioned to receive a patient attachment instrument therein such as, e.g., at least one of a bone screw, a bone pin, a bone spike, or other fixation devices. The patient attachment instrument may be used to couple the merge fixture 3400 to the anatomical feature of the patient anatomy. In the present embodiment, the merge fixture 3400 includes a pair of channels configured to receive a pair of bone screws 3416 therein, which affix the merge fixture 3400 to the anatomical feature in a known location and orientation relative to the patient anatomy. As such, the merge fixture 3400 provides a bone fixation feature which ensures the merge fixture 3400 remains securely positioned in the correct location and orientation relative to the patient anatomy.

Figure 35:
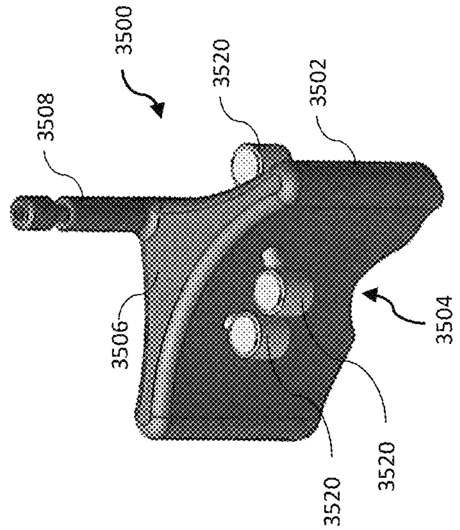
FIG. 35 illustrates a merge fixture according to another embodiment of the disclosure.

FIG. 35 illustrates a merge fixture 3500 according to another embodiment of the disclosure. The merge fixture 3500 includes a body 3502 having a first surface 3404 opposite a second surface 3506. The first surface 3504 is shaped and dimensioned to complement and engage an anatomical feature (e.g., vertebra) of the patient anatomy. An engagement portion 3508 extends away from the second surface 3506 and is configured to engage a dynamic reference base such as, e.g., DRB 1100. The merge fixture 3500 further includes a plurality of calibration phantoms 3520 attached to the body 3502 in known locations and orientations. The calibration phantoms 3520 are each configured to simulate a known BMD value corresponding to a known HU value in medical images. The plurality of calibration phantoms 3520 function in substantially the same way as described in detail with reference to FIGS. 20-30, the details of which are omitted herein for brevity. In the present embodiment, the calibration phantoms 3520 extend away from the body 3502. In alternative embodiments, at least one calibration phantom 3520 is disposed within the body 3502 between the first surface 3504 and the second surface 3506 thereof.

Figure 36:
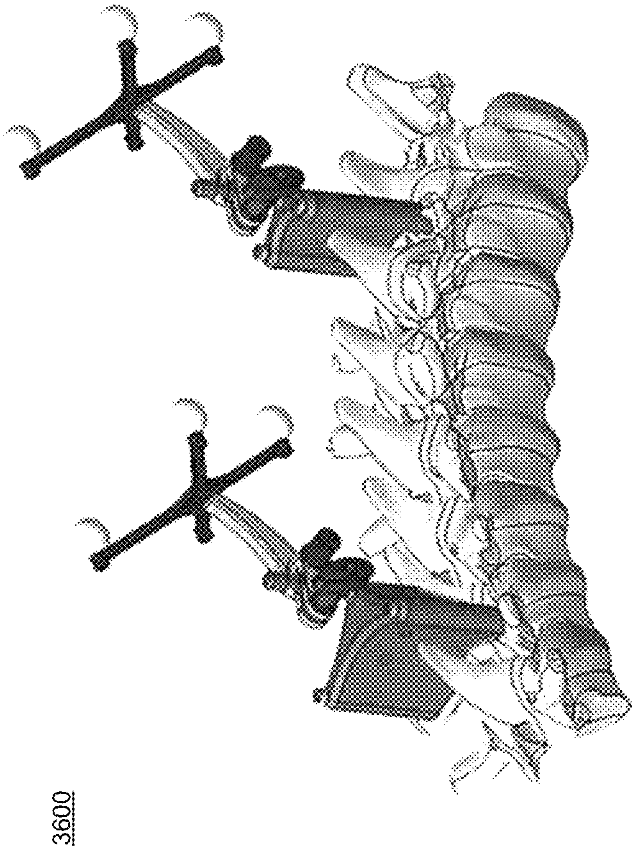
FIG. 36 illustrates a system including a plurality of merge fixtures affixed to the patient anatomy, in accordance with embodiments of the disclosure.
Figure 37:
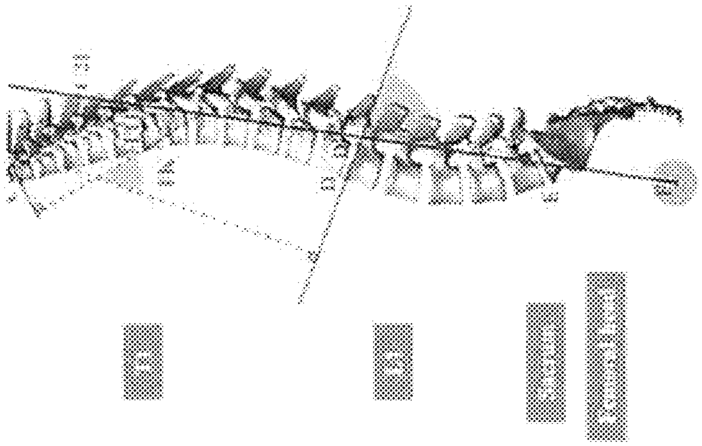
FIG. 37 illustrates exemplary spinal parameters determined by the system of FIG. 36, in accordance with embodiments of the disclosure.

FIG. 36 illustrates a system 3600 including a plurality of patient specific, merge fixtures configured to track the position and orientation of the patient anatomy during a spinal procedure. The plurality of merge fixtures may include one or more merge fixtures 3100, 3200, 3300, 3400, 3500 discussed herein. Each merge fixture may be shaped and dimensioned to complement a respective vertebra contour of the patient anatomy, such that each merge fixture is configured to matingly engage a respective vertebra in a specific position and orientation relative to the patient anatomy. As further shown, each merge fixture includes a unique DRB/array attached thereon, enabling the robotic system to distinguish between the plurality of merge fixtures during the surgical procedure. The robotic system may use the position and orientation information about vertebrae to calculate and/or display information to the user during the surgical procedure. For example, the robotic system may provide information including spinal alignment parameters, display 2D and/or 3D medical images of the spine, display or track progress toward a correction goal, dimensions of surgical implants, etc. FIG. 37 illustrates exemplary spinal alignment parameters that can be calculated from intra-operatively tracking the patient anatomy using the plurality of patient specific merge fixtures of the system 3600.

The disclosure therefore provides merge fixtures that move with the patient anatomy, and thereby maintain patient registration during the surgical procedure. This approach is beneficial because it eliminates the need for additional intra-operative fluoroscopy due to movement of the patient anatomy to update the known position and orientation of anatomical features thereof.

Figure 38:
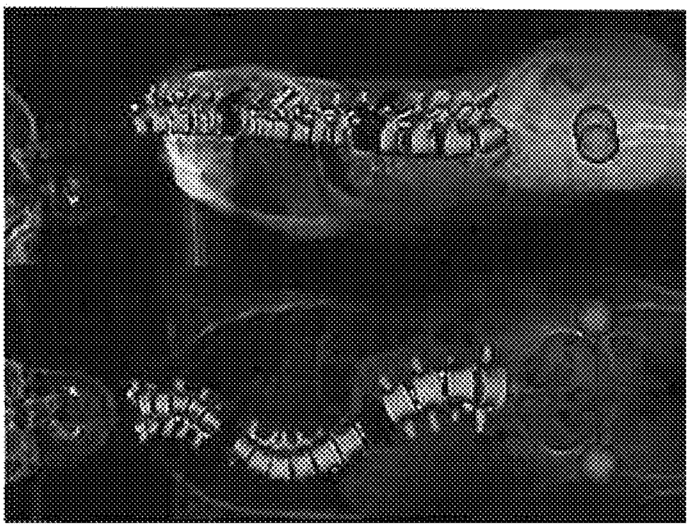
FIG. 38 illustrates the patient anatomy using a kinematic model, in accordance with embodiments of the disclosure.

In some implementations, one or more merge fixtures are configured to track the position and orientation of one or more anatomical features (e.g., vertebrae), and a kinematic model estimates the position and orientation of one or more anatomical features (e.g., vertebrae) that do not have a merge fixture affixed thereon. In some implementations, merge fixtures may be placed on the apical vertebrae and the neutral vertebrae, while the position and orientation of other vertebrae are estimated by the kinematic model. For example, four merge fixtures shaped and dimensioned to respectively engage four vertebra of the patient anatomy such as, e.g., T3, T12, L1, or L5, may be affixed to the patient anatomy. The one or more optical sensors, such as the camera 904, track the position and orientation of each merge fixture during the surgical procedure, respectively corresponding to the position and orientation of vertebrae during the surgical procedure. The robotic system may process the position and orientation data using the kinematic model, which estimates the position and orientation of the remaining vertebrae. FIG. 38 illustrates an example of intra-operative spinal alignment tracking using a kinematic model.

Figure 39:
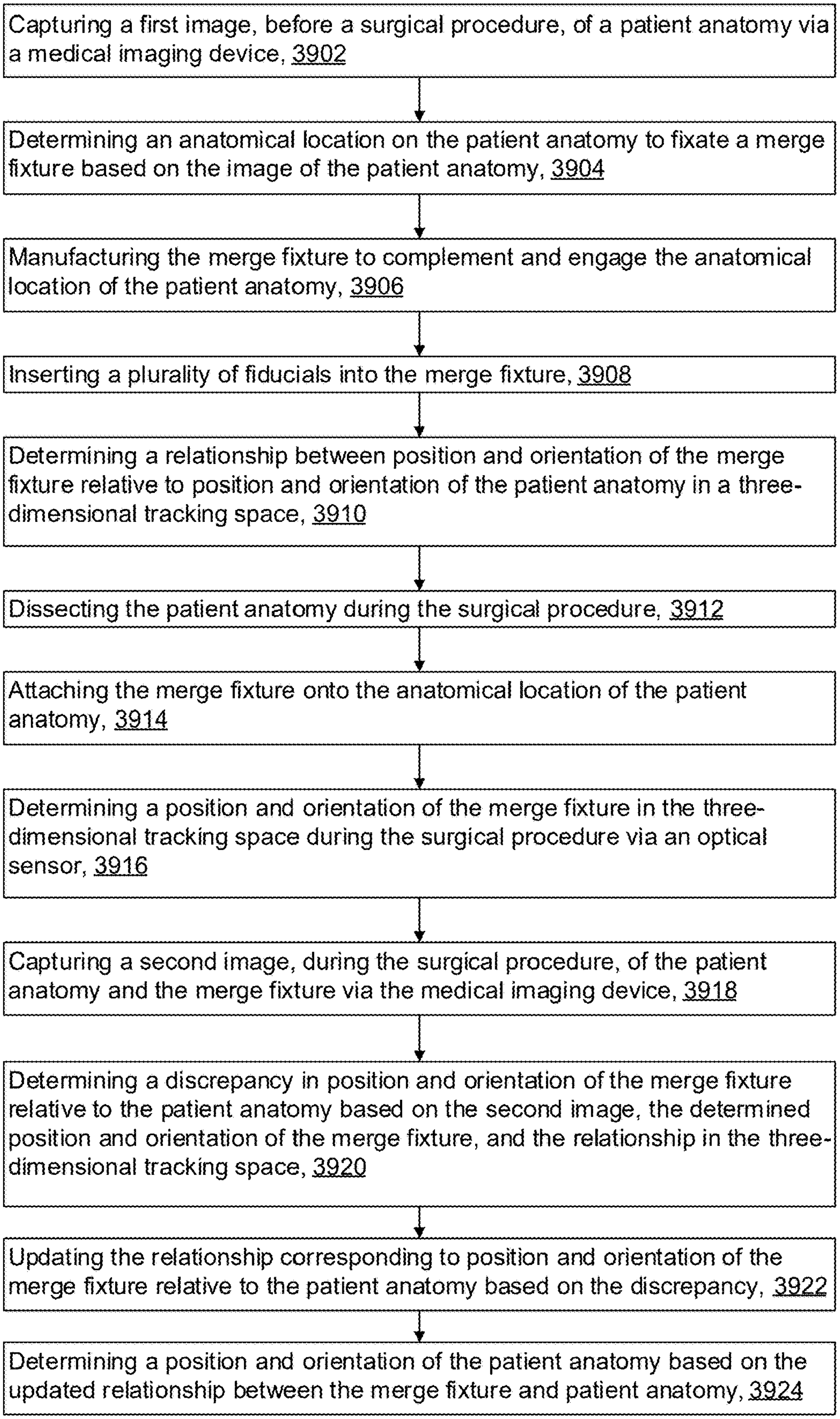
FIG. 39 illustrates a flow chart showing steps in a method for registering a patient anatomy using the fixtures described herein, in accordance with embodiments of the disclosure.
Figure 40:
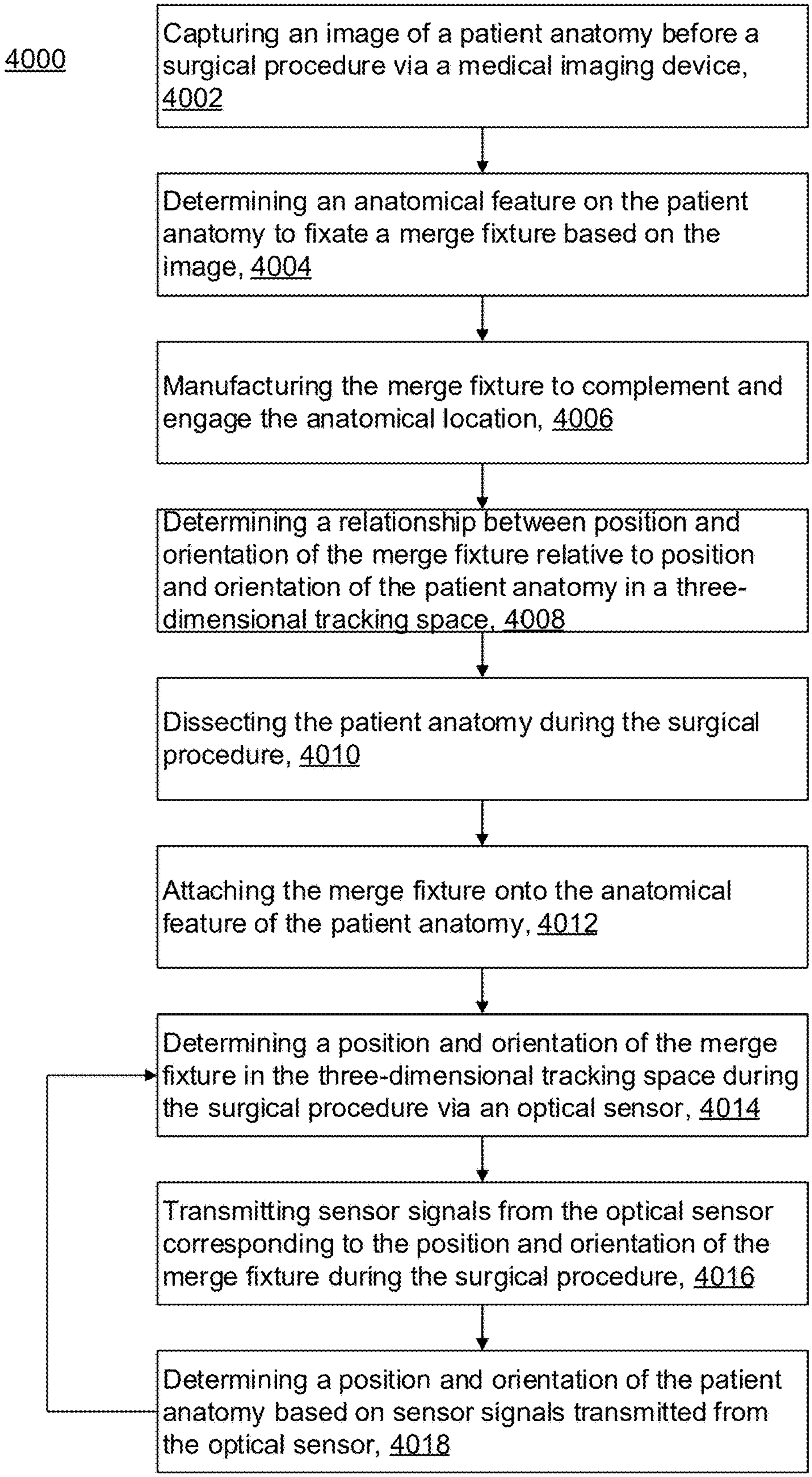
FIGS. 40-41 illustrate methods of making and using merge fixtures, in accordance with embodiments of the disclosure.
Figure 41:
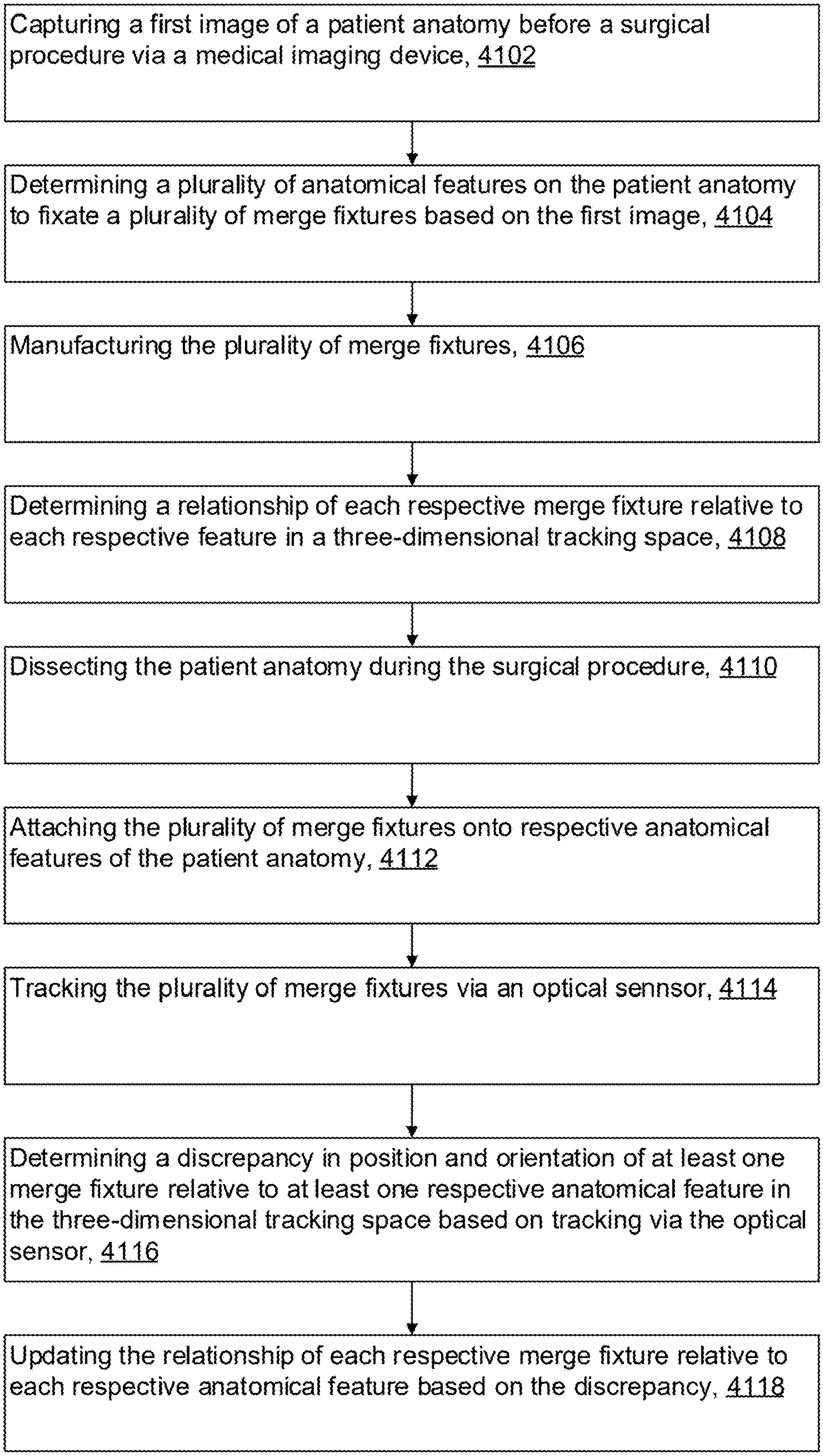

With reference to FIGS. 39-41, also provided herein are methods of using the fixtures and systems as described herein.

With reference to FIG. 39, a method 3900 for registering a patient anatomy using the fixtures described herein may include one or more operations as described herein. For example, a first operation 3902 may include capturing a first image, before a surgical procedure, of a patient anatomy via a medical imaging device such as, e.g., CT scanner 1304. At operation 3904, an anatomical feature or location on the patient anatomy is determined or selected to fixate a merge fixture based on the image of the patient anatomy. For example, a vertebra may be determined or selected for fixation of the merge fixture 3200 based on fluoroscopic images of the patient anatomy. At operation 3906, the merge fixture may be manufactured to complement and engage the anatomical feature of the patient anatomy. For example, the merge fixture 3200 may be manufactured via 3D printing to complement and engage the vertebra. At operation 3908, a plurality of fiducials may be inserted into the merge fixture. For example, a plurality of BBs 3212 may be inserted into a corresponding plurality of pockets in the body 3202 of the merge fixture 3200. At operation 3910, a relationship may be determined between the position and orientation of the merge fixture relative to position and orientation of the patient anatomy in a three-dimensional tracking space. For example, the relationship may be determined between the position and orientation of the merge fixture 3200 and components thereof, relative to the position and orientation of the vertebra in 3D tracking space based on the contour of the vertebra and merge fixture 3200. At operations 3912, the patient anatomy may be dissected during the surgical procedure. At operation 3914, the merge fixture may be attached onto the anatomical feature of the patient anatomy. For example, the patient anatomy may be dissected and the merge fixture 3200 may be attached onto the vertebra via one or more bone screws. At operation 3916, a position and orientation of the merge fixture may be determined in the three-dimensional tracking space during the surgical procedure via an optical sensor. For example, the position and orientation of the merge fixture 3200 may be determined using the camera 904 (FIG. 9) to track the DRB 1100 (FIG. 11) fixedly coupled to the merge fixture 3200. At operation 3918, a second image may be captured during the surgical procedure of the patient anatomy and the merge fixture via the medical imaging device. For example, intra-operative fluoroscopic images of the merge fixture 3200 may be captured via the CT scanner 1304. At operation 3920, a discrepancy in position and orientation of the merge fixture may be determined relative to the patient anatomy based on the second image, the determined position and orientation of the merge fixture, and the relationship in the three-dimensional space. For example, a discrepancy between the actual position and orientation of the merge fixture 3200 may be determined relative to the expected position and orientation of the merge fixture 3200 based on the second image and determined relationship of operation 3910. At operation 3922, if the discrepancy is determined, the relationship corresponding to position and orientation of the merge fixture relative to the patient anatomy may be updated based on the discrepancy. For example, the relationship may be updated to reflect the actual position and orientation of the merge fixture 3200 relative to the patient anatomy. At operation 3924, a position and orientation of the patient anatomy may be determined based on the updated relationship between the merge fixture and patient anatomy. For example, the patient anatomy may be re-registered based on the updated relationship between the merge fixture 3200 and the patient anatomy. In various embodiments, one or more of the foregoing steps may be performed in a different order than the order in which the operations are described herein.

With reference to FIG. 40, a method 4000 for registering patient anatomy during navigated and robotic spinal procedures without fluoroscopy using fixtures described herein may include one or more operations as described herein. For example, a first operation 4002 may include capturing a medical image of the patient anatomy before the surgical procedure via a medical imaging device. At operation 4004, an anatomical location on the patient anatomy to fixate the merge fixture is determined based on the medical image. At operation 4006, the merge fixture can be manufactured to complement and engage the anatomical location of the patient anatomy based on the medical image. Manufacturing the merge fixture may include an additive manufacturing process, or combination of processes, configured to deposit successive layers of material which collectively form the merge fixture. At operation 4008, a relationship between the position and orientation of the merge fixture relative to the position and orientation of the patient anatomy is determined in a 3D tracking space. At operation 4010, the patient is dissected during the surgical procedure to expose the anatomical location to fixate the merge fixture. At operation 4012, the merge fixture is attached onto the anatomical location of the patient anatomy. At operation 4014, during the surgical procedure, an optical sensor determines the position and orientation of the merge fixture in the 3D tracking space. At operation 4016, the optical sensor transmits sensor signals to the robot corresponding to the position and orientation of the merge fixture during the surgical procedure. At operation 4018, the robot determines the actual position and orientation of the patient anatomy based on the relationship between the merge fixture and the patient anatomy, and based on the sensor signals from the optical sensor. Operations 4014, 4016 and 4018 may repeat one or more times throughout the surgical procedure to update the position and orientation data as needed. In various embodiments, one or more of the foregoing steps may be performed in a different order than the order in which the operations are described herein.

With reference to FIG. 41, a method 4100 for registering a patient anatomy using the fixtures described herein may include one or more operations as described herein. For example, a first operation 4102 may include capturing a first image of a patient anatomy, before a surgical procedure, via a medical imaging device. For example, one or more fluoroscopic images may be captured. At operation 4104, a plurality of anatomical features on the patient anatomy to fixate a plurality of merge fixtures may be determined or selected based on the first image. For example, one or more vertebrae may be selected for affixation of a plurality of merge fixtures 3400. At operation 4106, the plurality of merge fixtures may be manufactured. For example, the plurality of merge fixtures 3400 may be manufactured via 3D printing, such that each merge fixture 3400 is shaped and dimensioned to complement the contour of a respective vertebra. At operation 4108, the relationship of each respective merge fixture relative to each respective anatomical feature is determined in a three-dimensional tracking space. For example, a relationship between the position and orientation of each merge fixture 3400 may be determined relative to a respective vertebra. At operation 4110, the patient anatomy may be dissected during the surgical procedure. At operation 4112, the plurality of merge fixtures may be attached onto respective anatomical features of the patient anatomy. For example, each of the merge fixtures 3400 may be attached onto a respective vertebra via one or more bone screws 3416. At operation 4114, the plurality of merge fixtures may be tracked via an optical sensor. For example, during the surgical procedure, the plurality of merge fixtures 3400 may be tracked via the camera 904. At operation 4116, a discrepancy in position and orientation of at least one merge fixture may be determined relative to at least one respective anatomical feature in the three-dimensional tracking space based on tracking via the optical sensor. For example, a discrepancy in the actual position and orientation of one of the merge fixtures 3400 may be determined relative to the respective vertebra, based on the expected position determined via the relationship of operation 4108 and on measurements from the camera 904 corresponding to the actual position and orientation during the surgical procedure. At operation 4118, the relationship of each respective merge fixture may be updated relative to each respective anatomical feature based on the discrepancy. For example, the relationship may be updated between the position and orientation of one of the merge fixtures 3600, and the position and orientation of the respective vertebra based on the discrepancy determined via the camera 904. In various embodiments, one or more of the foregoing steps may be performed in a different order than the order in which the operations are described herein.

The methods described herein and depicted in FIGS. 39-41 may be similarly applicable to any of the merge fixtures described herein.

In the above description of various embodiments of present inventive concepts, it is to be understood that the terminology used herein is for the purpose of describing particular embodiments only and is not intended to be limiting of present inventive concepts. Unless otherwise defined, all terms (including technical and scientific terms) used herein have the same meaning as commonly understood by one of ordinary skill in the art to which present inventive concepts belong. It will be further understood that terms, such as those defined in commonly used dictionaries, should be interpreted as having a meaning that is consistent with their meaning in the context of this specification and the relevant art and will not be interpreted in an idealized or overly formal sense unless expressly so defined herein.

When an element is referred to as being "connected", "coupled", "responsive", or variants thereof to another element, it can be directly connected, coupled, or responsive to the other element or intervening elements may be present. In contrast, when an element is referred to as being "directly connected", "directly coupled", "directly responsive", or variants thereof to another element, there are no intervening elements present. Like numbers refer to like elements throughout. Furthermore, "coupled", "connected", "responsive", or variants thereof as used herein may include wirelessly coupled, connected, or responsive. As used herein, the singular forms "a", "an" and "the" are intended to include the plural forms as well, unless the context clearly indicates otherwise. Well-known functions or constructions may not be described in detail for brevity and/or clarity. The term "and/or" includes any and all combinations of one or more of the associated listed items.

It will be understood that although the terms first, second, third, etc. may be used herein to describe various elements/operations, these elements/operations should not be limited by these terms. These terms are only used to distinguish one element/operation from another element/operation. Thus, a first element/operation in some embodiments could be termed a second element/operation in other embodiments without departing from the teachings of present inventive concepts. The same reference numerals or the same reference designators denote the same or similar elements throughout the specification.

As used herein, the terms "comprise", "comprising", "comprises", "include", "including", "includes", "have", "has", "having", or variants thereof are open-ended, and include one or more stated features, integers, elements, steps, components or functions but does not preclude the presence or addition of one or more other features, integers, elements, steps, components, functions or groups thereof. Furthermore, as used herein, the common abbreviation "e.g.", which derives from the Latin phrase "exempli gratia," may be used to introduce or specify a general example or examples of a previously mentioned item, and is not intended to be limiting of such item. The common abbreviation "i.e.", may be used to specify a particular item from a more general recitation.

Example embodiments are described herein with reference to block diagrams and/or flowchart illustrations of computer-implemented methods, apparatus (systems and/or devices) and/or computer program products. It is understood that a block of the block diagrams and/or flowchart illustrations, and combinations of blocks in the block diagrams and/or flowchart illustrations, can be implemented by computer program instructions that are performed by one or more computer circuits. These computer program instructions may be provided to a processor circuit of a general purpose computer circuit, special purpose computer circuit, and/or other programmable data processing circuit to produce a machine, such that the instructions, which execute via the processor of the computer and/or other programmable data processing apparatus, transform and control transistors, values stored in memory locations, and other hardware components within such circuitry to implement the functions/acts specified in the block diagrams and/or flowchart block or blocks, and thereby create means (functionality) and/or structure for implementing the functions/acts specified in the block diagrams and/or flowchart block(s).

These computer program instructions may also be stored in a tangible computer-readable medium that can direct a computer or other programmable data processing apparatus to function in a particular manner, such that the instructions stored in the computer-readable medium produce an article of manufacture including instructions which implement the functions/acts specified in the block diagrams and/or flowchart block or blocks. Accordingly, embodiments of present inventive concepts may be embodied in hardware and/or in software (including firmware, resident software, micro-code, etc.) that runs on a processor such as a digital signal processor, which may collectively be referred to as "circuitry," "a module" or variants thereof.

It should also be noted that in some alternate implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated. Finally, other blocks may be added/inserted between the blocks that are illustrated, and/or blocks/operations may be omitted without departing from the scope of inventive concepts. Moreover, although some of the diagrams include arrows on communication paths to show a primary direction of communication, it is to be understood that communication may occur in the opposite direction to the depicted arrows.

Although several embodiments of inventive concepts have been disclosed in the foregoing specification, it is understood that many modifications and other embodiments of inventive concepts will come to mind to which inventive concepts pertain, having the benefit of teachings presented in the foregoing description and associated drawings. It is thus understood that inventive concepts are not limited to the specific embodiments disclosed hereinabove, and that many modifications and other embodiments are intended to be included within the scope of the appended claims. It is further envisioned that features from one embodiment may be combined or used with the features from a different embodiment(s) described herein. Moreover, although specific terms are employed herein, as well as in the claims which follow, they are used only in a generic and descriptive sense, and not for the purposes of limiting the described inventive concepts, nor the claims which follow. The entire disclosure of each patent and patent publication cited herein is incorporated by reference herein in its entirety, as if each such patent or publication were individually incorporated by reference herein. Various features and/or potential advantages of inventive concepts are set forth in the following claims.

What is claimed is:

1. A system comprising:

a medical imaging device comprising an x-ray source and an x-ray detector configured to generate a plurality of images based on x-rays received at the x-ray detector from the x-ray source;

a fixture coupled to the medical imaging device between the x-ray source and the x-ray detector;

a calibration phantom coupled to the fixture and configured to calibrate the medical imaging device based on known, simulated bone mineral density (BMD) of material disposed therein, wherein the calibration phantom comprises a first material having a first simulated BMD, and a second material having a second simulated BMD; and a medical navigation system operatively coupled with the medical imaging device, the fixture, and the calibration phantom, wherein the medical navigation system is configured to register the plurality of images from the medical imaging device to a three-dimensional tracking space a patient specific merge fixture including a body having at least one surface shaped and dimensioned to complement and engage the contour of an anatomical feature of the patient anatomy, wherein the contour of the anatomical feature is derived from 3D medical images of the patient anatomy captured by the medical image device.

2. The system of claim 1, wherein each of the first material and the second material of the calibration phantom comprises at least one of hydroxyapatite, plastic, polymer, metal, or a combination of these materials.

3. The system of claim 1, wherein the fixture includes at least one of a registration fixture, a patient attachment instrument, or combinations thereof.

4. The system of claim 1, wherein the fixture includes a registration fixture comprising:

a frame configured to be coupled with the medical imaging device;

an engagement portion disposed in the frame and configured to couple the calibration phantom with the frame; and an x-ray opaque fiducial pattern disposed on the frame and operatively coupled with the medical imaging device.

5. The system of claim 4, wherein the calibration phantom comprises:

a first calibration phantom shaped and dimensioned to contain the first material therein and to engage a first portion of the engagement portion of the fixture; and a second calibration phantom shaped and dimensioned to contain the second material therein and to engage a second portion of the engagement portion of the fixture.

6. The system of claim 4, wherein the registration fixture is configured to create at least one shadow corresponding to the x-ray opaque fiducial pattern, the first material, the second material, or combinations thereof, in at least one of the plurality of images from the medical imaging device.

7. The system of claim 4, wherein the x-ray opaque fiducial pattern comprises a plurality of radiopaque markers disposed in the frame of the registration fixture.

8. The system of claim 7, wherein the plurality of radiopaque markers comprises a first set of radiopaque markers disposed in the frame and arranged in a first plane, and a second set of radiopaque markers disposed in the frame and arranged in a second plane offset from the first plane.

9. The system of claim 1, wherein the medical imaging device includes a computed tomography (CT) scanner comprising an arm having the x-ray source at a first end thereof, and the x-ray detector at a second end thereof opposite the first end.

10. The system of claim 1, wherein the merge fixture comprises an engagement portion configured to couple the calibration phantom with the body of the merge fixture.

11. The system of claim 1, further comprising a dynamic reference base including a plurality of reflective fiducials and a clamp, wherein the merge fixture comprises a post extending superiorly from the second surface and configured to be received within the clamp.

12. The system of claim 1, wherein the calibration phantom is at least partially disposed within the body of the merge fixture.

13. The system of claim 1, wherein the merge fixture comprises an aperture disposed in the body and configured to matingly engage at least one of a bone screw, a bone pin, a bone spike, or combinations thereof, to fixedly coupled the merge fixture with the vertebrae.

14. The system of claim 1, wherein the merge fixture comprises a light emitting diode (LED) configured to transmit electromagnetic signals therefrom, and wherein the medical navigation system comprises an optical sensor configured to determine a location of the merge fixture in the three-dimensional tracking space based on electromagnetic signals transmitted from the LED to the optical sensor.

* * * * *